US010358606B2

(12) United States Patent
Song et al.

(10) Patent No.: US 10,358,606 B2
(45) Date of Patent: Jul. 23, 2019

(54) PROCESS FOR PRODUCING AROMATICS, P-XYLENE AND TEREPHTHALIC ACID

(71) Applicants: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

(72) Inventors: Qi Song, Shanghai (CN); Junlin Zheng, Shanghai (CN); Dejin Kong, Shanghai (CN); Xuan Xu, Shanghai (CN); Xiaolan Qi, Shanghai (CN); Xiangdong Jiang, Shanghai (CN); Deqin Yang, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

( * ) Notice: Subject to any disclaimer, the term of this patent is extended or adjusted under 35 U.S.C. 154(b) by 0 days.

(21) Appl. No.: 15/738,063

(22) PCT Filed: Jun. 17, 2016

(86) PCT No.: PCT/CN2016/000315
§ 371 (c)(1),
(2) Date: Dec. 19, 2017

(87) PCT Pub. No.: WO2016/201955
PCT Pub. Date: Dec. 22, 2016

(65) Prior Publication Data
US 2018/0282631 A1   Oct. 4, 2018

(30) Foreign Application Priority Data

| Jun. 19, 2015 | (CN) | 2015 1 0344592 |
| Jun. 19, 2015 | (CN) | 2015 1 0345647 |
| Jun. 19, 2015 | (CN) | 2015 1 0345806 |
| Jun. 19, 2015 | (CN) | 2015 1 0345812 |
| Jun. 19, 2015 | (CN) | 2015 1 0345823 |
| Jun. 19, 2015 | (CN) | 2015 1 0345824 |
| Jun. 19, 2015 | (CN) | 2015 1 0345846 |
| Jun. 19, 2015 | (CN) | 2015 1 0345909 |
| Jun. 19, 2015 | (CN) | 2015 1 0345987 |

(51) Int. Cl.
| C10G 3/00 | (2006.01) |
| C07C 1/207 | (2006.01) |
| C07C 63/26 | (2006.01) |
| B01J 29/40 | (2006.01) |
| C07C 15/04 | (2006.01) |
| C07C 15/06 | (2006.01) |
| C07C 15/08 | (2006.01) |

(52) U.S. Cl.
CPC .............. C10G 3/48 (2013.01); B01J 29/40 (2013.01); C07C 1/207 (2013.01); C07C 63/26 (2013.01); C07C 15/04 (2013.01); C07C 15/06 (2013.01); C07C 15/08 (2013.01); C07C 2523/10 (2013.01); C07C 2523/28 (2013.01); C07C 2523/30 (2013.01); C07C 2527/053 (2013.01); C07C 2527/12 (2013.01); C07C 2529/40 (2013.01); C10G 2300/1014 (2013.01); C10G 2400/30 (2013.01); Y02P 30/20 (2015.11)

(58) Field of Classification Search
CPC ........... C07C 1/20; C07C 1/207; C07C 15/02; C07C 15/04; C07C 15/06; C07C 15/08; C07C 2523/10; C10G 3/48; C10G 2300/1014; C10G 3/49; C10G 2400/30; B01J 29/40
See application file for complete search history.

(56) References Cited

U.S. PATENT DOCUMENTS

2009/0227823 A1   9/2009   Huber et al.
2011/0257416 A1  10/2011   Cortright et al.

FOREIGN PATENT DOCUMENTS

CN   104230615 A   12/2014
JP   2010202548   *   9/2010   ............... C07C 1/20

OTHER PUBLICATIONS

JP 2010202548, Tsutsui Toshio, Apparatus fort he production of levulinic acid, apparatus for separating levulinic acid, and apparatus for producing hydrocarbon from levulinic acid, English translation 23 pages (Year: 2010).*
Tahsiro, Y., et al., A new strategy for the preparation of terephthalic acid by the aerobic oxidaton of p-xylene using N-hydroxyphthalimide as a catalyst, 2001, Adv. Synth. Catal, vol. 343 No. 2, pp. 220-225 (Year: 2010).*

(Continued)

Primary Examiner — Yate' K Cutliff
(74) Attorney, Agent, or Firm — Novick, Kim & Lee, PLLC; Allen Xue

(57) ABSTRACT

The present invention relates to a process for producing aromatics, p-xylene and terephthalic acid. The process for producing aromatics comprises a step of contacting an oxygen-containing raw material with an aromatization catalyst, under aromatization reaction conditions, to produce aromatics. The process for producing aromatics has an advantage of high yield of carbon as aromatics.

24 Claims, No Drawings

(56) References Cited

OTHER PUBLICATIONS

Katherine Bourzac, "A startup's catalytic process converts biomass directly into components of gasoline", MIT Technology Review, Mar. 29, 2010.

David Martin Alonso et al., "Direct conversion of cellulose to levulinic acid and gamma-valerolactone using solid acid catalysts", Catalysis Science & Technology, 2013,3, pp. 927-931.

Stephanie G. Wettstein et al., "Production of levulinic acid and gamma-valerolactone (GVL) from cellulose using GVL as a solvent in biphasic systems", Energy Environmental Science, 2012, 5, pp. 8199-8203.

Yosuke Muranaka et al., "Effective Production of Levulinic Acid from Biomass through Pretreatment Using Phosphoric Acid, Hydrochloric Acid, or Ionic Liquid", Industrial & Engineering Chemistry Resarch, 2014, 53 (29), pp. 11611-11621.

Yun Ma, "Advances in SO2-4/MxOy solid superacid catalysts", Applied Chemical Industry, vol. 43, No. 10, Oct. 2014, pp. 1879-1890.

\* cited by examiner

PROCESS FOR PRODUCING AROMATICS, P-XYLENE AND TEREPHTHALIC ACID

TECHNICAL FIELD

The present invention relates to a process for producing aromatics, in particular a process for producing BTX aromatics with a high yield of carbon. The present invention further relates to a process for producing p-xylene and terephthalic acid based on the process for producing aromatics.

BACKGROUND

Aromatics are important fundamental raw materials for petrochemical industry, which are widely used in the fields of polyester, chemical fiber, rubber and the like. Benzene, toluene, and xylene are the three most widely used aromatics, which are generalized as light aromatics or BTX aromatics. Currently, the worldwide aromatic production depends mainly on the non-renewable fossil resource, whilst the production cost of aromatics is more and more increased due to the limited reserve and non-renewability of the fossil resource. In addition, the increasing exploitation and utilization of fossil resource result in abundant discharge of greenhouse gases, leading to more and more severe environmental problems. Therefore, developing the technique of producing aromatics (especially BTX aromatics) from renewable resources is of importance.

As renewable resources, production of aromatics using a biomass material as raw material is one of the most interested technical projects currently. There are reports about converting biomass material into aromatics, and also reports about platform compounds useful thereof (e.g., see Katherine Bourzac, From biomass to chemicals in one step, MIT Technology Review, 2010 March 29; CN104230615A; US20090227823 and US20110257416A1).

However, the general defect of the prior arts is a relatively low carbon availability during the conversion from biomass material to aromatics, which demonstrates poor utilization efficiency of biomass, resulting in a relatively low yield of carbon for the aromatics (especially BTX aromatics).

SUMMARY OF THE INVENTION

Regarding the situation introduced above, the inventors of the present invention deem it desirable to develop a process for producing aromatics, which shows improved biomass utilization efficiency and thus achieves improved yield of carbon for aromatics (in particular improved yield of carbon for BTX aromatics), when being used, for example, during the conversion from biomass material to aromatics.

The inventors of the present invention have discovered through hard study that the problems present in the prior art above can be solved by using a specific oxygen-containing compound as a platform compound in a process for producing aromatics using biomass material as a raw material, and thus have achieved the present invention.

Specifically, the present invention involves the following aspects of contents.

1. A process for producing aromatics, comprising a step of contacting an oxygen-containing raw material with an aromatization catalyst to produce aromatics, under aromatization reaction conditions, wherein the oxygen-containing raw material has the structural formula (I):

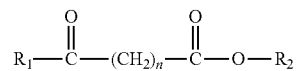

In formula (I), $R_1$ is selected from the group consisting of optionally substituted $C_{1-8}$ linear or branched alkyl and optionally substituted $C_{2-8}$ linear or branched alkenyl, preferably optionally substituted $C_{1-4}$ linear or branched alkyl, more preferably methyl, $R_2$ is selected from the group consisting of hydrogen and optionally substituted $C_{1-10}$ linear or branched alkyl, preferably selected from the group consisting of hydrogen and optionally substituted $C_{1-5}$ linear or branched alkyl, more preferably hydrogen, n is a positive integer of 1 to 6, preferably a positive integer of 1 to 4, more preferably 2.

2. The process according to any one of the preceding aspects, wherein the aromatization reaction conditions comprise: a reaction temperature of 300 to 800 degrees C., preferably 300 to 650 degrees C., a reaction pressure of 0.1 to 10.0 MPa, preferably 0.5 to 6.0 MPa, a hydrogen pressure of 0.1 to 5 MPa (gage pressure), preferably 0.5 to 4 MPa, and a weight hourly space velocity (WHSV) of oxygen-containing raw material 0.3 to 10 $\text{hour}^{-1}$, preferably 0.3 to 5 $\text{hour}^{-1}$.

3. The process according to any one of the preceding aspects, wherein the oxygen-containing raw material is derived from a biomass material, preferably derived from one or more of xylitol, glucose, cellobiose, cellulose, hemicellulose and lignin, or derived from one or more of paper manufacture sludge, waste paper, bagasse, glucose, wood, corn cob, corn stover and straw stover.

4. The process according to any one of the preceding aspects, wherein the aromatization catalyst is one or more selected from the group consisting of solid acid catalysts, preferably one or more selected from the group consisting of molecular sieve, solid super acid and composite metal oxide.

5. The process according to any one of the preceding aspects, wherein the molecular sieve is one or more selected from the group consisting of ZSM-type molecular sieve (in particular one or more selected from the group consisting of ZSM-5, ZSM-11, ZSM-22, ZSM-23 and ZSM-38), Y-type molecular sieve, beta-type molecular sieve, L-type molecular sieve, MCM-type molecular sieve (in particular one or more selected from the group consisting of MCM-22 and MCM-41), in particular one or more selected from the group consisting of ZSM-5, Y-type molecular sieve, beta-type molecular sieve and MCM-41, more in particular ZSM-5 or M/ZSM-5 (wherein M is selected from the group consisting of Zn, Ga, Sn or a combination thereof).

6. The process according to any one of the preceding aspects, wherein the molecular sieve is a molecular sieve composition, comprising the components of:
A) 20 to 80 parts by weight (preferably 30 to 70 parts by weight) of the molecular sieve,
B) 20 to 80 parts by weight (preferably 30 to 70 parts by weight) of a binder (preferably one or more selected from the group consisting of silica sol, pseudo-boehmite, alumina, acid treated clay, kaolin, montmorillonite, and bentonite, more preferably one or more selected from the group consisting of pseudo-boehmite, alumina, and silica sol),
C) 0 to 10 parts by weight (preferably 0.01 to 10 parts by weight, more preferably 0.01 to 6 parts by weight) of an auxiliary, wherein the auxiliary is one or more selected from the group consisting of Na, Ca, K, Be, Mg, Ba, V, Nb, Cr, Mo, W, Mn, Re, Fe, Co, Ni, Cu, Zn, Ga, Ru, Pd, Pt, Ag, B, Al, Sn, P, Sb, La and Ce, preferably one or more selected from the group consisting of Ca, K, Mg, Cr, Mo, Fe, Ni, Cu, Zn, Ga, Ru, Pd, Pt, Ag, B, Sn, P, La and Ce, more preferably one or more selected from the group consisting of Zn, Ga and Sn.

7. The process according to any one of the preceding aspects, wherein the ZSM-type molecular sieve has a molar ratio of Si to Al, calculated as $SiO_2/Al_2O_3$=10 to 500, preferably $SiO_2/Al_2O_3$=15 to 100 or 15 to 200, the Y-type molecular sieve has a molar ratio of Si to Al, calculated as $SiO_2/Al_2O_3$=2 to 70, preferably $SiO_2/Al_2O_3$=3 to 50 or 5 to 50, the beta-type molecular sieve has a molar ratio of Si to Al, calculated as $SiO_2/Al_2O_3$=10 to 150, preferably $SiO_2/Al_2O_3$=15 to 65 or 50 to 100, the L-type molecular sieve has a molar ratio of Si to Al, calculated as $SiO_2/Al_2O_3$=5 to 100, preferably $SiO_2/Al_2O_3$=6 to 35, and the MCM-type molecular sieve has a molar ratio of Si to Al, calculated as $SiO_2/Al_2O_3$=20 to 250, preferably $SiO_2/Al_2O_3$=32 to 150.

8. The process according to any one of the preceding aspects, wherein the solid super acid is one or more selected from the group consisting of Lewis acid supported solid super acid, solid super acid as inorganic metal salt/Lewis acid composite and solid super acid as sulfated metal oxide.

9. The process according to any one of the preceding aspects, wherein the support of the Lewis acid supported solid super acid is one or more of selected from the group consisting of solid oxide of an element from Group IIIA and solid oxide of an element from Group IVA, of the periodic table, preferably one or more of selected from the group consisting of $SiO_2$, $B_2O_3$ and $Al_2O_3$, the Lewis acid of the Lewis acid supported solid super acid is one or more selected from the group consisting of halide (preferably fluoride) of an element from Group VB, halide (preferably fluoride) of an element from Group IIIA and halide (preferably fluoride) of an element from Group VA of the periodic table of elements, preferably one or more selected from the group consisting of halide (preferably fluoride) of an element from Group VB and halide (preferably fluoride) of an element from Group VA of the periodic table of elements, further preferably one or more selected from the group consisting of $PF_3$, $AsF_3$, $SbF_3$, $BiF_3$, $SbF_5$, $TaF_3$, $VF_3$ and $NbF_3$, the Lewis acid supported solid super acid is preferably one or more selected from the group consisting of $SbF_5/SiO_2$—$Al_2O_3$, $PF_3/Al_2O_3$—$B_2O_3$, $AsF_3/Al_2O_3$—$B_2O_3$, $SbF_3/Al_2O_3$—$B_2O_3$, $BiF_3/Al_2O_3$—$B_2O_3$, $TaF_3/Al_2O_3$—$B_2O_3$, $VF_3/Al_2O_3$—$B_2O_3$ and $NbF_3/Al_2O_3$—$B_2O_3$, the inorganic metal salt of the solid super acid as inorganic metal salt/Lewis acid composite is one or more selected from the group consisting of inorganic acid salt (preferably haloid acid salt, more preferably hydrochloride) of a metal element from Group IB, inorganic acid salt (preferably haloid acid salt, more preferably hydrochloride) of a metal element from Group IIB, inorganic acid salt (preferably haloid acid salt, more preferably hydrochloride) of a metal element from Group VII and inorganic acid salt (preferably haloid acid salt, more preferably hydrochloride) of a metal element from Group VIII of the periodic table of elements, preferably $CuCl_2$, the Lewis acid of the solid super acid as inorganic metal salt/Lewis acid composite is one or more selected from the group consisting of halide (preferably chloride) of an element from Group VB, halide (preferably chloride) of an element from Group IIIA and halide (preferably chloride) of an element from Group VA of the periodic table of elements, preferably one or more selected from the group consisting of halide (preferably chloride) of an element from Group IIIA of the periodic table of elements, preferably $AlCl_3$, the solid super acid as inorganic metal salt/Lewis acid composite is preferably $AlCl_3$—$CuCl_2$, the metal oxide of the solid super acid as sulfated metal oxide is oxide A of a metal element from Group IVB of the periodic table of elements (preferably one or more selected from the group consisting of $ZrO_2$ and $TiO_2$) or is oxide B obtained by modifying the oxide A with one or more modifying elements selected from the group consisting of metal element from Group IIIA (in the form of oxide), metal element from Group VIIB (in the form of oxide), noble metal element from Group VIII (in the form of metal elementary substance), base metal element from Group VIII (in the form of oxide), metal element from Group VIB (in the form of oxide) and lanthanide metal element (in the form of oxide) of the periodic table of elements (the modifying element being preferably one or more selected from the group consisting of Fe, Pt, Re, Al, W, Cr, Mo and Mn), the solid super acid as sulfated metal oxide is preferably one or more selected from the group consisting of $SO_4^{2-}/ZrO_2$, $S_2O_8^{2-}/ZrO_2$, $SO_4^{2-}/TiO_2$, $SO_4^{2-}/ZrO_2$—$Fe_3O_4$, $Pt/SO_4^{2-}/TiO_2$, $SO_4^{2-}/TiO_2$—$ZrO_2$, $SO_4^{2-}/TiO_2$—$Al_2O_3$, $SO_4^{2-}/TiO_2$—$WO_3$, $SO_4^{2-}/ZrO_2$—$Fe_2O_3$—$Cr_2O_3$, $SO_4^{2-}/ZrO_2$—$WO_3$, $SO_4^{2-}/TiO_2$—$MoO_3$ and $SO_4^{2-}/ZrO_2$—$Fe_2O_3$—$MnO_2$.

10. The process according to any one of the preceding aspects, wherein in the Lewis acid supported solid super acid, the Lewis acid is supported in an amount of 1 to 30 wt %, preferably 1 to 15 wt %, relative to the weight of the support, in the solid super acid as inorganic metal salt//Lewis acid composite, the weight ratio between the inorganic metal salt and the Lewis acid is 1-30:100, preferably 1-15:100, in the solid super acid as sulfated metal oxide, the metal oxide has a sulfated rate of 0.5-25 wt %, preferably 1-8 wt %, in the oxide B, the weight ratio of the modifying element in the form of oxide (calculated as oxide) to the oxide A is 0.1-25:100, preferably 0.5-10:100, and the weight ratio of the modifying element in the form of metal elementary substance (calculated as metal) to the oxide A is 0.1-15:100, preferably 0.3-6:100.

11. The process according to any one of the preceding aspects, wherein the composite metal oxide is a composite oxide of oxide C of a metal element from Group IVB of the periodic table of elements (preferably one or more selected from the group consisting of $ZrO_2$ and $TiO_2$, more preferably $ZrO_2$) and one or more oxides D selected from the group consisting of oxide of a metal element from Group IIIA, oxide of a metal element from Group VII, oxide of a metal element from Group VIB and lanthanide metal element of the periodic table of elements (preferably one or more selected from the group consisting of $B_2O_3$, $Al_2O_3$, $MnO_2$, $Cr_2O_3$, $CrO_3$, $MoO_3$, $WO_3$, $La_2O_3$ and $CeO_2$, more preferably one or more selected from the group consisting of $MnO_2$, $MoO_3$, $WO_3$, $La_2O_3$ and $CeO_2$), preferably a composite oxide of $ZrO_2$ and one or more oxides D selected from the group consisting of $MnO_2$, $Mo_2O_3$, $WO_3$, $La_2O_3$ and $CeO_2$.

12. The process according to any one of the preceding aspects, wherein the ratio of oxide C to oxide D is 60-99.9:0.1-40, preferably 60-99:1-40, calculated in parts by weight.

13. The process according to any one of the preceding aspects, further comprising a step of catalytically converting the biomass material, to provide the oxygen-containing raw material.

14. A process for producing p-xylene, comprising the steps of:
a step of producing aromatics according to any one of the preceding aspects; and
a step of separating p-xylene from the aromatics.
15. A process for producing terephthalic acid, comprising the steps of:
a step of producing p-xylene according to any one of the preceding aspects; and
a step of converting p-xylene into terephthalic acid.

TECHNICAL EFFECT

According to one embodiment, the process for producing aromatics according to the present invention can, e.g., during the conversion process from biomass to aromatics, increase the carbon availability, reduce the proportion of carbon in the biomass material converted into gaseous carbon and carbon deposition, increase the yield of carbon for aromatics (in particular the yield of carbon for BTX aromatics) and finally increase the selectivity to BTX aromatics. For example, the yield of carbon as BTX aromatics can be up to 93% or more, with a minimum of 30% or more, and the selectivity to BTX aromatics can be up to 95% or more, using the process for producing aromatics according to the present invention.

EMBODIMENTS

The embodiments of the present invention are illustrated below, whilst it should be understood that the protection scopes of the present invention are not restricted thereto; instead, the protection scopes are defined by the claims attached.

The publications, patent applications, patents and other references cited in the specification are all incorporated herein by reference. Unless otherwise defined, the scientific and technical terms used in the specification have meanings same as those conventionally known by those skilled in the art. In case of any confliction occurs, including any definitions, those skilled should understand referring to the present specification.

When the specification describes material, process, part, device or equipment modified with terms of "known by those skilled in the art" or "conventionally known in the art" or the like, the terms should be understood not only according to the conventional knowledge known up to the application date, but also further taking into account those not conventionally known currently yet whilst will be transformed into ones deemed as useful for similar purposes.

In addition, the various ranges cited in the specification each comprise the terminals thereof, unless otherwise specified. In addition, when a range, one or more preferable ranges, or a plurality of preferable upper limit values and preferable lower limit values are disclosed for an amount, a concentration or any other value or parameter, they should be deemed as disclosing all ranges formed with arbitrary pairs of any upper limits or preferable values of the ranges with any lower limits or preferable values of the ranges, despite these value pairs being disclosed one by one or not.

In the context of the specification, unless otherwise defined specifically or the meaning provided exceeds the conventional understandings by those skilled, then any hydrocarbon or any group derived from a hydrocarbon having 3 or more carbon atoms (for example propyl, propoxy, butyl, butane, butylene, butenyl, hexane and the like) should be understood to mean same with or without modification by a prefix of "n-". For example, the term propyl is generally understood to represent n-propyl, while butyl is generally understood to represent n-butyl.

In the context of the specification, unless otherwise defined specifically, conversion, yield and selectivity denote respectively a single-pass conversion, a single-pass yield and a single-pass selectivity.

In the context of the specification, phrase "optionally substituted" denotes being optionally substituted by one or more (e.g., 1-3, 1-2 or 1) substituents selected from the group consisting of $C_{1-6}$ linear or branched alkyl optionally substituted by one or more carboxyl or hydroxyl, $C_{2-6}$ linear or branched alkenyl optionally substituted by one or more carboxyl or hydroxyl, $C_{2-6}$ linear or branched alkynyl optionally substituted by one or more carboxyl or hydroxyl, $C_{3-10}$ cycloalkyl optionally substituted by one or more carboxyl or hydroxyl, $C_{6-10}$ aryl optionally substituted by one or more carboxyl or hydroxyl, carboxyl and hydroxyl.

In the context of the specification, term "halogen" denotes fluorine, chlorine, bromine and iodine.

In the context of the specification, without specific indication, all of the percentages, parts, ratios and the like are calculated by weight, unless the calculation by weight does not conform to the conventional understanding by those skilled in the art.

One embodiment according to the present invention provides a process for producing aromatics, comprising a step of contacting an oxygen-containing raw material with an aromatization catalyst to produce aromatics, under aromatization reaction conditions (sometimes called as a contact step hereinafter).

According to one embodiment of the present invention, the oxygen-containing raw material has structural formula (I).

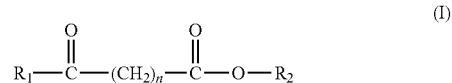

(I)

According to one embodiment of the present invention, in formula (I), $R_1$ is selected from the group consisting of optionally substituted $C_{1-8}$ linear or branched alkyl and optionally substituted $C_{2-8}$ linear or branched alkenyl, preferably optionally substituted $C_{1-4}$ linear or branched alkyl, more preferably methyl.

According to one embodiment of the present invention, in formula (I), $R_2$ is selected from the group consisting of hydrogen and optionally substituted $C_{1-10}$ linear or branched alkyl, preferably selected from the group consisting of hydrogen and optionally substituted $C_{1-5}$ linear or branched alkyl, more preferably hydrogen.

According to one embodiment of the present invention, in formula (I), n is a positive integer of 1 to 6, preferably a positive integer of 1 to 4, more preferably 2.

According to one embodiment of the present invention, the oxygen-containing raw material is levulinic acid.

According to one embodiment of the present invention, in the aromatization reaction, the reaction temperature is generally 100 to 1000 degrees C., in particular 300 to 800 degrees C., preferably 300 to 650 degrees C.

According to one embodiment of the present invention, in the aromatization reaction, the reaction pressure is generally 0.1 to 20.0 MPa (gage pressure), in particular 0.1 to 10.0 MPa (gage pressure), preferably 0.5 to 6.0 MPa (gage pressure).

According to one embodiment of the present invention, in the aromatization reaction, the hydrogen pressure is 0.1 to 5 MPa, preferably 0.5 to 4 MPa (gage pressure).

According to one embodiment of the present invention, in the aromatization reaction, the WHSV of the oxygen-containing raw material is generally 0.1 to 20 hour$^{-1}$, in particular 0.3 to 10 hour$^{-1}$, preferably 0.5 to 5 hour$^{-1}$.

According to one embodiment of the present invention, the oxygen-containing raw material is derived from a biomass material. Examples of the biomass material can comprise those conventionally used to produce aromatics in the art, specifically, e.g., xylitol, glucose, cellobiose, cellulose, hemicellulose and lignin, etc. These biomass materials can be used alone, or can be used as a combination of two or more thereof.

According to another embodiment of the present invention, paper manufacture sludge, waste paper, bagasse, glucose, wood, corn cob, corn stover and straw stover, and the like, can be specifically provided as further examples of the biomass material. These biomass materials can be used alone, or can be used as a combination of two or more thereof. Here, in the biomass material, the content of cellulose is generally 30-99%, the content of hemicellulose is generally 0-50%, and the content of lignin is generally 0 or 1-40%, by weight percent.

According to one embodiment of the present invention, the method for deriving the oxygen-containing raw material using a biomass material as raw material is not restricted specifically, while those conventionally known in the art can be used. For example, the method for derivation can comprise, for instance, a step of catalytically converting the biomass material (e.g., hydrolysis deoxidation, catalytic hydrolysis of inorganic acid, catalytic hydrolysis of organic acid, catalytic hydrolysis of solid acid, catalytic hydrolysis of molecular sieve, supercritical hydrolysis, catalytic partial oxidation or catalysis with metal chloride) to produce the oxygen-containing raw material (in particular levulinic acid) (e.g., see, Direct conversion of cellulose to levulinic acid and gamma-valerolactone using solid acid catalysts, Catal. Sci. Technol., 2013, 3, 927-931; Production of levulinic acid and gamma-valerolactone (GVL) from cellulose using GVL as a solvent in biphasic systems, Energy Environ. Sci., 2012, 5, 8199-8203; Effective Production of Levulinic Acid from Biomass through Pretreatment Using Phosphoric Acid, Hydrochloric Acid, or Ionic Liquid, Ind. Eng. Chem. Res., 2014, 53 (29), pp 11611-11621).

According to one embodiment of the present invention, examples of the aromatization catalyst can comprise solid acid catalyst, more specifically, for example, molecular sieve, solid super acid and composite metal oxide and the like. These aromatization catalysts can be used alone, or can be used as a combination of two or more thereof.

According to one embodiment of the present invention, for better technical effects to be achieved by the present invention, examples of the aromatization catalyst can comprise preferably molecular sieve.

According to one embodiment of the present invention, examples of the molecular sieve can comprise ZSM-type molecular sieve, Y-type molecular sieve, beta-type molecular sieve, L-type molecular sieve and MCM-type molecular sieve, in particular ZSM-5, Y-type molecular sieve, beta-type molecular sieve and MCM-41, more particularly ZSM-5. These molecular sieves can be used alone, or can be used as a combination of two or more thereof. These molecular sieves can be used directly as a commercially available product or can be produced according to a method known from prior art.

According to one embodiment of the present invention, examples of the molecular sieve can comprise specifically ZSM-5, ZSM-11, ZSM-22, ZSM-23 and ZSM-38, in particular ZSM-5 (or HZSM-5). Here, the ZSM-type molecular sieve has a molar ratio of Si to Al, calculated as $SiO_2/Al_2O_3$, of generally 10 to 500, preferably 15 to 200 or 15 to 100. Different categories (comprising those having different molar ratios of Si to Al) of ZSM-type molecular sieves can be used alone, or can be used as a combination of two or more thereof.

According to one embodiment of the present invention, the Y-type molecular sieve has a molar ratio of Si to Al, calculated as $SiO_2/Al_2O_3$, of generally 2 to 70, preferably 3 to 50 or 5 to 50. Different categories (comprising those having different molar ratios of Si to Al) of Y-type molecular sieves can be used alone, or can be used as a combination of two or more thereof.

According to one embodiment of the present invention, the beta-type molecular sieve has a molar ratio of Si to Al, calculated as $SiO_2/Al_2O_3$, of generally 10 to 150, preferably 15 to 65 or 50 to 100. Different categories (comprising those having different molar ratios of Si to Al) of beta-type molecular sieves can be used alone, or can be used as a combination of two or more thereof.

According to one embodiment of the present invention, the L-type molecular sieve has a molar ratio of Si to Al, calculated as $SiO_2/Al_2O_3$, of generally 5 to 100, preferably 6 to 35. Different categories (comprising those having different molar ratios of Si to Al) of L-type molecular sieves can be used alone, or can be used as a combination of two or more thereof.

According to one embodiment of the present invention, examples of the MCM-type molecular sieve can comprise specifically MCM-22 and MCM-41. Here, the MCM-type molecular sieve has a molar ratio of Si to Al, calculated as $SiO_2/Al_2O_3$, of generally 20 to 250, preferably 32 to 150. Different categories (comprising those having different molar ratios of Si to Al) of MCM-type molecular sieves can be used alone, or can be used as a combination of two or more thereof.

According to one embodiment of the present invention, the molecular sieve is used in the form of a molecular sieve composition A, comprising: a1) 20 to 80 parts by weight of the molecular sieve, b1) 20 to 80 parts by weight of a binder, and c1) 0 to 10 parts by weight of an auxiliary. In particular, the molecular sieve composition A comprises: a1) 30 to 70 parts by weight of the molecular sieve, b1) 30 to 70 parts by weight of a binder, and c1) 0.01 to 10 parts by weight (or 0.01 to 6 parts by weight) of an auxiliary.

According to another embodiment of the present invention, the molecular sieve is used in the form of a molecular sieve composition B, comprising: a2) 90 to 99.99 parts by weight of the molecular sieve, and c2) 0.01 to 10 parts by weight of an auxiliary. In particular, the molecular sieve composition B comprises: a2) 95 to 99.99 parts by weight of the molecular sieve, and c2) 0.01 to 5 parts by weight of an auxiliary.

According to one embodiment of the present invention, these molecular sieve compositions can be used directly as a commercially available product or can be produced according to a method known from prior art. Specifically, as a method of producing the molecular sieve composition, the following method can be mentioned, for example: mixing and kneading molecular sieve, binder and, if needed, extrusion aid, pore-expanding agent and water to provide a mixture, extruding and shaping, followed by drying at a temperature of 100-200 degree Celsius for 1-24 h, and calcining at a temperature of 400-700 degree Celsius for 1-10 h. Examples of the extrusion aid can comprise those conventionally used in the art, such as sesbania powder, polyethylene glycol or sodium carboxymethylcellulose and the like; while examples of the pore-expanding agent can comprise those conventionally used in the art, such as citric acid, oxalic acid or ethylenediamine tetraacetic acid and the like. In general, the extrusion aid and pore-expanding agent are added in a total amount not greater than 10 wt % of the total weight of the mixture. As required, acid can also be added during shaping. Examples of the acid can comprise inorganic acid, acetic acid or an aqueous solution thereof and the like, in particular an aqueous solution of nitric acid, sulfuric acid or phosphoric acid. In general, the aqueous solution of acid is added in an amount of 50-90 wt % of the total weight of the mixture.

According to one embodiment of the present invention, the auxiliary can be incorporated during the production of the molecular sieve composition or after the production of the molecular sieve composition; or alternatively can be incorporated firstly into the molecular sieve followed by producing the molecular sieve composition using the thus obtained molecular sieve, without specific restriction thereto. Examples of a method of incorporating the auxiliary can comprise those methods conventionally used in the art, in particular ion-exchange method or immersion method. In the methods, auxiliary is generally used in the form of a precursor. Accordingly, examples of the precursor of metal auxiliary can comprise nitrate, sulfate, acetate or chloride salt and the like of the metal; the examples the precursor of boron auxiliary can comprise boric acid or borax; while examples of the precursor of phosphorus auxiliary can comprise diammonium phosphate and so on.

According to one embodiment of the present invention, examples of the binder can comprise those binders conventionally used in the art for producing a molecular sieve composition, more specifically, for example, silica sol, pseudo-boehmite, alumina, acid treated clay, kaolin, montmorillonite and bentonite and the like, in particular alumina (in particular γ-alumina), pseudo-boehmite and montmorillonite and the like. These binders can be used alone, or can be used as a combination of two or more thereof.

According to one embodiment of the present invention, examples of the auxiliary can comprise Na, Ca, K, Be, Mg, Ba, V, Nb, Cr, Mo, W, Mn, Re, Fe, Co, Ni, Cu, Zn, Ga, Ru, Pd, Pt, Ag, B, Al, Sn, P, Sb, La and Ce, in particular Ca, K, Mg, Cr, Mo, Fe, Ni, Cu, Zn, Ga, Ru, Pd, Pt, Ag, B, Sn, P, La and Ce and the like. These auxiliaries can be used alone, or can be used as a combination of two or more thereof. The auxiliary is preferably Zn, Ga, Sn or a combination thereof.

According to one embodiment of the present invention, examples of the molecular sieve can comprise particularly M/ZSM-5, wherein M is selected from the group consisting of Zn, Ga, Sn or a combination thereof. The molecular sieve or a molecular sieve composition comprising the molecular sieve is especially useful as the aromatization catalyst. The molecular sieves can be used directly as a commercially available product or can be produced according to a method known from prior art.

According to one embodiment of the present invention, examples of the solid super acid can comprise those conventionally used as solid acid catalyst, more specifically, for example, Lewis acid supported solid super acid, solid super acid as inorganic metal salt/Lewis acid composite and solid super acid as sulfated metal oxide. These solid super acids can be used alone, or can be used as a combination of two or more thereof. These solid super acids can be used directly as a commercially available product or can be produced according to a method known from prior art.

According to one embodiment of the present invention, the Lewis acid supported solid super acid comprises a support and a Lewis acid on the support. Examples of the support can comprise solid oxide of an element from Group IIIA and solid oxide of an element from Group IVA of the periodic table of elements, in particular $SiO_2$, $B_2O_3$ and $Al_2O_3$. These supports can be used alone, or can be used as a combination of two or more thereof. Examples of Lewis acid can comprise halide of an element from Group VB, halide of an element from Group IIIA and halide of an element from Group VA of the periodic table of elements, in particular halide of an element from Group VB and halide of an element from Group VA of the periodic table of elements, more particularly $PF_3$, $AsF_3$, $SbF_3$, $BiF_3$, $SbF_5$, $TaF_3$, $VF_3$ and $NbF_3$. Here, fluoride is preferably used as a halide. These Lewis acids can be used alone, or can be used as a combination of two or more thereof. More specifically, examples of the Lewis acid supported solid super acid can comprise $SbF_5/SiO_2$—$Al_2O_3$, $PF_3/Al_2O_3$—$B_2O_3$, $AsF_3/Al_2O_3$—$B_2O_3$, $SbF_3/Al_2O_3$—$B_2O_3$, $BiF_3/Al_2O_3$—$B_2O_3$, $TaF_3/Al_2O_3$—$B_2O_3$, $VF_3/Al_2O_3$—$B_2O_3$ and $NbF_3/Al_2O_3$—$B_2O_3$. These Lewis acid supported solid super acids can be used alone, or can be used as a combination of two or more thereof.

According to one embodiment of the present invention, in the Lewis acid supported solid super acid, the Lewis acid is supported in an amount of 1 to 30 wt %, preferably 1 to 15 wt %, relative to the weight of the support.

According to one embodiment of the present invention, the solid super acid as inorganic metal salt/Lewis acid composite is a composite consisting of an inorganic metal salt and a Lewis acid. Examples of the inorganic metal salt can comprise inorganic acid salt of a metal element from Group IB, inorganic acid salt of a metal element from Group IIB, inorganic acid salt of a metal element from Group VII and inorganic acid salt of a metal element from Group VIII of the periodic table of elements. Here, examples of the inorganic acid salt can particularly comprise haloid acid salt, especially hydrochloride. These inorganic metal salts can be used alone, or can be used as a combination of two or more thereof. Examples of the Lewis acid can comprise halide of an element from Group VB, halide of an element from Group IIIA and halide of an element from Group VA of the periodic table of elements, in particular halide of an element from Group IIIA of the periodic table of elements. Here, chloride is preferably used as a halide. These Lewis acids can be used alone, or can be used as a combination of two or more thereof. The solid super acid as inorganic metal salt/Lewis acid composite is preferably $AlCl_3$—$CuCl_2$. These solid super acids as inorganic metal salt/Lewis acid composite can be used alone, or can be used as a combination of two or more thereof.

According to one embodiment of the present invention, in the solid super acid as inorganic metal salt/Lewis acid composite, the weight ratio between the inorganic metal salt and the Lewis acid is 1-30:100, preferably 1-15:100.

According to one embodiment of the present invention, in the solid super acid as sulfated metal oxide, examples of the metal oxide can comprise oxide of a metal element from Group IVB of the periodic table of elements (called as oxide A hereinafter), or oxide obtained by modifying the oxide A with a modifying element comprising a metal element from Group IIIA, a metal element from Group VIIB, a noble metal element from Group VIII, a base metal element from Group VIII, a metal element from Group VIB or lanthanide metal element of the periodic table of elements (called as oxide B hereinafter). These metal oxides can be used alone, or can be used as a combination of two or more thereof. These modifying elements can be used alone, or can be used as a combination of two or more thereof. Examples of the oxide A can comprise $ZrO_2$, $TiO_2$ or a combination thereof. Examples of the modifying element can comprise Fe, Pt, Re, Al, W, Cr, Mo, Mn or a combination thereof. In the oxide B, the metal element from Group IIIA of the periodic table of elements is generally present in the form of an oxide, the metal element from Group VIIB is generally present in the form of an oxide, the noble metal element from Group VIII is generally present in the form of a metal elementary substance, the base metal element from Group VIII is generally present in the form of an oxide, the metal element from Group VIB is generally present in the form of an oxide, and the lanthanide metal element is generally present in the form of an oxide. Examples of the solid super acid as sulfated metal oxide can particularly comprise $SO_4^{2-}/ZrO_2$, $S_2O_8^{2-}/ZrO_2$, $SO_4^{2-}/TiO_2$, $SO_4^{2-}/ZrO_2$—$Fe_3O_4$, $Pt/SO_4^{2-}/TiO_2$, $SO_4^{2-}/TiO_2$—$ZrO_2$, $SO_4^{2-}/TiO_2$—$Al_2O_3$, $SO_4^{2-}/TiO_2$—$WO_3$, $SO_4^{2-}/ZrO_2$—$Fe_2O_3$—$Cr_2O_3$, $SO_4^{2-}/ZrO_2$—$WO_3$, $SO_4^{2-}/TiO_2$—$MoO_3$ and $SO_4^{2-}/ZrO_2$—$Fe_2O_3$—$MnO_2$. The aforementioned solid super acids as sulfated metal oxide can be used alone, or can be used as a combination of two or more thereof.

According to one embodiment of the present invention, in the oxide B, the weight ratio of the modifying element in the form of oxide (calculated as oxide) to the oxide A is generally 0.1-25:100, preferably 0.5-10:100, and the weight ratio of the modifying element in the form of metal elementary substance (calculated as metal) to the oxide A is generally 0.1-15:100, preferably 0.3-6:100.

According to one embodiment of the present invention, in the solid super acid as sulfated metal oxide, the metal oxide generally has a sulfated rate of 0.5-25 wt %, preferably 1-8 wt %, According to one embodiment of the present invention, the method of producing the solid super acid as sulfated metal oxide is not restricted specifically, for which those conventionally known in the art can be used, specifically, e.g., precipitation-immersion method (for example, see the document "Progress in $SO_4^{2-}/M_xO_y$ solid superacid catalysts, Applied Chemical Industry, 2014, vol 43, 1879-1883").

According to one embodiment of the present invention, examples of the composite metal oxide can comprise a composite oxide of oxide of a metal element from Group IVB of the periodic table of elements with another oxide (called as oxide D hereinafter). Examples of the oxide C can comprise $ZrO_2$, $TiO_2$ or a combination thereof, in particular $ZrO_2$. Examples of the oxide D can comprise oxide of a metal element from Group IIIA, oxide of a metal element from Group VII, oxide of a metal element from Group VIB, of the periodic table of elements, and oxide of a lanthanide metal element, and the like, more specifically $B_2O_3$, $Al_2O_3$, $MnO_2$, $Cr_2O_3$, $CrO_3$, $MoO_3$, $WO_3$, $La_2O_3$ and $CeO_2$ and the like, in particular $MnO_2$, $MoO_3$, $WO_3$, $La_2O_3$ and $CeO_2$ and the like. These oxides D can be used alone, or can be used as a combination of two or more thereof. Examples of the composite metal oxide can comprise a composite oxide of $ZrO_2$ with one or more oxides D selected from the group consisting of $MnO_2$, $Mo_2O_3$, $WO_3$, $La_2O_3$ and $CeO_2$.

According to one embodiment of the present invention, in the composite metal oxide, the ratio of oxide C to oxide D is generally 60-99.9:0.1-40, preferably 60-99:1-40, calculated in parts by weight.

According to one embodiment of the present invention, the composite metal oxide can be used directly as a commercially available product or can be produced according to a method known from prior art. Examples of the method of producing the composite metal oxide can comprise immersion method or precipitation method, and the like. More specifically, for example, an immersion method comprises immersing tungsten, molybdenum, cerium, lanthanum or manganese as a saline solution onto zirconia, throwing away the spare liquid after 12 to 48 hours of immersion, drying at a temperature of 100 to 200 degree Celsius, evaporating out of water to leave the active components, followed by treatment by calcining and activating procedures to provide the composite metal oxide; or alternatively, a precipitation method comprises adding simultaneously an aqueous solution of metal salt of tungsten, molybdenum, cerium, lanthanum or manganese, an aqueous solution of a metal salt of zirconium and an aqueous ammonia as precipitant to generate a solid precipitation, washing, filtrating and drying the precipitation generated, and calcining at a temperature of 400 to 600 degree Celsius to provide the composite metal oxide.

According to one embodiment of the present invention, the contact step can be carried out in one or more reactors. Examples of the reactor can comprise bed reactor, in particular fixed bed reactor, fluidized bed reactor, ebullated bed reactor or a combination thereof. At this point, the reactor can be operated in batched, or continuously, without specific restriction.

According to an embodiment of the present invention, the contact step can be carried out under inert gas atmosphere or reducing gas atmosphere. Examples of the inert gas atmosphere can comprise $N_2$, $CO_2$, He, Ar or a combination thereof. Examples of the reducing gas atmosphere can comprise CO, $H_2$ or a combination thereof.

According to one embodiment of the present invention, aromatics are produced as a product according to the aforementioned process for producing aromatics. In general, in the aromatics product, the content of BTX aromatics is 60% or more by weight of the total weight, in particular, benzene content being 5.0-10.0%, toluene content being 30.0-40.0%, xylene content being 280.0-40.0%, whilst the balance being non-aromatic hydrocarbons and heavy aromatics. The heavy aromatics denote C9 and higher aromatics.

After producing the aromatics as a product according to the process for producing aromatics of the present invention, p-xylene can be separated from the aromatic product. Thus, the present invention further relates to a process for producing p-xylene, comprising a step of producing aromatics according to the process for producing aromatics of the present invention; and a step of separating p-xylene from the aromatics.

According to one embodiment of the present invention, the method of separating p-xylene from the aromatics is not specifically restricted, while those conventionally known in the art can be used directly.

According to one embodiment of the present invention, terephthalic acid can be produced using p-xylene produced according to the present invention introduced above as a raw material. Thus, the present invention further relates to a process for producing terephthalic acid, comprising a step of producing p-xylene according to the aforementioned process for producing p-xylene of the present invention; and a step of converting the p-xylene into terephthalic acid.

According to one embodiment of the present invention, the method of converting p-xylene into terephthalic acid is not specifically restricted, while those conventionally known in the art can be used directly.

EXAMPLES

The present invention will be further illustrated in more detail using the Examples below, whilst the present invention is not restricted to these Examples.

In order to illustrate the result of the present invention, in the context of the specification, the yield of carbon as aromatics and the yield of carbon as BTX aromatics are used to illustrate the result of tests, wherein the yield of carbon as BTX aromatics is the main comparative indicator. The yield of carbon as aromatics and the yield of carbon as BTX aromatics are calculated according to the formulae below.

The yield carbon as aromatics (%)=weight of aromatics as a reaction product (g)/carbon weight of the oxygen-containing raw material as a reaction raw material*100%

The yield carbon as BTX aromatics (%)=weight of BTX aromatics as a reaction product (g)/carbon weight of the oxygen-containing raw material as a reaction raw material*100%

An example for calculation is as follows:

100 g of levulinic acid is used as the oxygen-containing raw material, which comprises 51.7 g of carbon; then, if 38.8 g of aromatics is obtained after reaction, the yield of carbon as aromatics is 75%. The 38.8 g of aromatics comprises 19.4 g of BTX aromatics, then the yield of carbon as BTX aromatics is 50%.

Comparative Example I-1

The raw material was 1 kg of bagasse, comprising 52% of dry basis cellulose and 27% of hemicellulose. The bagasse was mixed sufficiently with 0.19 kg of ZSM-5 ($SiO_2$/$Al_2O_3$=60), and reacted in a rapid fluidized bed at a temperature of 600 degree Celsius for 240 s, to provide 138 g of total aromatics, having a composition showed in table I-1, wherein benzene, toluene and xylene comprised 48.4 wt % of the aromatics product.

TABLE I-1 composition of the aromatization product

| | Non-aromatic hydrocarbons | Benzene | Toluene | Ethylbenzene | P-xylene | M-xylene | O-xylene | C9 aromatics | $C_{10}^+$ aromatics |
|---|---|---|---|---|---|---|---|---|---|
| Composition/wt % | <1 | 12.9 | 21.8 | 1.3 | 3.4 | 7.1 | 3.2 | 4.1 | 45.3 |
| Output/g | | 1.2 | 17.8 | 30.1 | 1.8 | 4.7 | 9.8 | 4.4 | 5.7 | 62.5 |

Comparative Example I-2

The raw material was 1 kg of pine saw dust, comprising 41.9% of dry basis cellulose and 22.8% of hemicellulose. The pine saw dust was mixed sufficiently with 0.19 kg of ZSM-5 ($SiO_2$/$Al_2O_3$=60), and reacted in a rapid fluidized bed at a temperature of 600 degree Celsius for 240 s, to provide 129 g of total aromatics, having a composition showed in table I-2, wherein benzene, toluene and xylene comprised 49.1 wt % of the aromatics product.

TABLE I-2 composition of the aromatization product

| | Non-aromatic hydrocarbons | Benzene | Toluene | Ethylbenzene | P-xylene | M-xylene | O-xylene | C9 aromatics | $C_{10}^+$ aromatics |
|---|---|---|---|---|---|---|---|---|---|
| Composition/wt % | <1 | 12.3 | 22.4 | 1.4 | 3.7 | 7.6 | 3.1 | 4.5 | 44.1 |
| Output/g | | 1.1 | 15.9 | 28.9 | 1.8 | 4.8 | 9.8 | 4.0 | 5.8 | 56.9 |

Example I-1

The raw material was 1 t of paper manufacture sludge, having a dry basis cellulose content of 61%. The paper manufacture sludge was mixed under sufficient stirring with 3.5 t of 3% aqueous solution of sulfuric acid, stirred and reacted under 3.0 MPa at a temperature of 205 degree Celsius for 25 min to complete the acidolysis process. The liquid phase product was separated to provide 275 kg of levulinic acid and 104.5 kg of formic acid. 104.5 kg of formic acid was decomposed to provide 4.5 kg of hydrogen.

The levulinic acid product obtained was further converted on an aromatization catalyst. The catalyst contained 60% of L-type zeolite with a molar ratio of Si:Al of 35 and balance of alumina supporter. The reaction was conducted at a temperature of 450 degree Celsius under a reaction pressure of 0.8 MPa and a space velocity of 0.5 $h^{-1}$. The conversion of levulinic acid was 100%. The hydrocarbon product was obtained in a total amount of 136.7 kg, with a composition showed in I-3. The content of aromatics was 125.5 kg, and benzene, toluene and xylene comprised 87.9% by weight of the product. The total amount of hydrogen created was 1.3 kg, the yield of carbon as aromatics was 88.2%, and the yield of carbon as BTX aromatics was 73.9%.

zeolite (with a molar ratio of Si:Al of 32), 3% of $SiO_2$ and 17% of $Al_2O_3$. The reaction was conducted at a temperature of 450 degree Celsius under a reaction pressure of 0.8 MPa and a space velocity of 0.5 hW. The conversion of methyl tetrahydrofuran was 100%. The hydrocarbon product was obtained in a total amount of 166.2 kg, with a composition showed in I-4. The content of aromatics was 157.1 kg, and benzene, toluene and xylene comprised 80.2% by weight of the product. The total amount of hydrogen created was 2.6 kg, the yield of carbon as aromatics was 85.6%, and the yield of carbon as BTX aromatics was 66.1%.

TABLE I-3

| | composition of the aromatization product | | | | | | | | |
|---|---|---|---|---|---|---|---|---|---|
| | Non-aromatic hydrocarbons | Benzene | Toluene | Ethylbenzene | P-xylene | M-xylene | O-xylene | C9 aromatics | $C_{10}^+$ aromatics |
| Composition/wt % | 8.2 | 7.4 | 31.8 | 3.8 | 9.6 | 19.1 | 9.0 | 7.5 | 3.6 |
| Output/KG | 11.2 | 10.1 | 43.4 | 5.2 | 13.1 | 26.1 | 12.4 | 10.2 | 5.0 |

Example I-2

The raw material was 1 t of bagasse, having a dry basis cellulose content of 52% and a hemicellulose content of 27%. The bagasse was comminuted sufficiently, mixed under stirring with 3.5 t of 1.5% aqueous solution of hydrochloric acid, then added with 1.2 kg of iron trichloride, and the mixed solution was reacted under 1.0 MPa at a temperature of 180 degree Celsius by microwave heating for 10 min to complete the acidolysis process. The liquid phase product was separated to provide 248 kg of levulinic acid, 95 kg of formic acid and 135 kg of furfural. 95 kg of formic acid was decomposed to provide 4.1 kg of hydrogen.

On a 0.5% Ru/C catalyst, with a reaction pressure of 1.2 MPa, a reaction temperature of 130 degree Celsius, a molar ratio of hydrogen/levulinic acid of 10, and a space velocity of levulinic acid of 0.3 $h^{-1}$, the conversion of levulinic acid was 89%, the molar selectivity to γ-valerolactone was 4.5%, and the molar selectivity to methyl tetrahydrofuran was 94.3%. Through hydrogenation reaction, 248 kg of levulinic acid generated 8.5 kg γ-valerolactone and 154.1 kg of methyl tetrahydrofuran. On a 10% Ni-0.2% Pd/$Al_2O_3$ catalyst, with a reaction pressure of 2.0 MPa, a reaction temperature of 190 degree Celsius, a molar ratio of hydrogen/furfural of 30, and a space velocity of furfural of 0.5 $h^{-1}$, the conversion of furfural was 94%, and the selectivity to 2-methyl tetrahydrofuran was 90.3%. Through hydrogenation reaction, 135 kg of furfural generated 102 kg of methyl tetrahydrofuran. The hydrogen used for hydrogenations of levulinic acid and furfural was obtained from the decomposition of formic acid.

The hydrogenation product of levulinic acid containing predominantly methyl tetrahydrofuran and the hydrogenation product of furfural predominantly containing methyl tetrahydrofuran were further converted on an aromatization catalyst. The catalyst contained 80% of MCM-22 type

TABLE I-4

| | composition of the aromatization product | | | | | | | | |
|---|---|---|---|---|---|---|---|---|---|
| | Non-aromatic hydrocarbons | Benzene | Toluene | Ethylbenzene | P-xylene | M-xylene | O-xylene | C9 aromatics | $C_{10}^+$ aromatics |
| Composition/wt % | 5.5 | 6.8 | 29.3 | 3.7 | 9.5 | 18.4 | 8.9 | 13.7 | 4.2 |
| Output/KG | 9.1 | 11.3 | 48.7 | 6.1 | 15.8 | 30.8 | 14.8 | 22.7 | 6.9 |

Example I-3

The raw material was 1 t of municipal waste paper, having a dry basis cellulose content of 92.1%. The municipal waste paper was comminuted sufficiently, mixed under stirring with 3.5 t of 3.5% aqueous solution of sulfuric acid, then added with 13 kg of sodium sulfite, and the mixed solution was reacted under stirring under 3.0 MPa at a temperature of 205 degree Celsius for 30 min to complete the acidolysis process. The liquid phase product was separated to provide 464.4 kg of levulinic acid and 197.6 kg of formic acid. 197.6 kg of formic acid was decomposed to provide 8.5 kg of hydrogen.

The levulinic acid was further converted on an aromatization catalyst. The catalyst contained 60% of ZSM-5 (a molar ratio of Si:Al of 38), 10% of ZSM-23 type zeolite (a molar ratio of Si:Al of 25) and 30% of $SiO_2$. The reaction was conducted at a temperature of 450 degree Celsius under a reaction pressure of 0.8 MPa and a space velocity of 0.5 $h^{-1}$. The conversion of levulinic acid was 100%. The hydrocarbon product was obtained in a total amount of 213.0 kg, with a composition showed in I-5. The content of aromatics was 187.5 kg, and benzene, toluene and xylene comprised 86.3% by weight of the product. The total amount of hydrogen created was 3.4 kg, the yield of carbon as aromatics was 78.1%, and the yield of carbon as BTX aromatics was 64.3%.

TABLE I-5

| | Non-aromatic hydrocarbons | Benzene | Toluene | Ethylbenzene | P-xylene | M-xylene | O-xylene | C9 aromatics | $C_{10}^+$ aromatics |
|---|---|---|---|---|---|---|---|---|---|
| Composition/wt % | 12.0 | 9.1 | 37.3 | 3.5 | 6.7 | 13.1 | 6.2 | 8.6 | 3.5 |
| Output/KG | 25.6 | 19.4 | 79.4 | 7.5 | 14.3 | 27.9 | 13.2 | 18.3 | 7.4 |

Example I-4

The raw material was 1 t of pine saw dust, having a dry basis cellulose content of 41.9% and a hemicellulose content of 22.8%. The pine saw dust was comminuted sufficiently, mixed under stirring with 3.5 t of 2.8% aqueous solution of sulfuric acid, and the mixed solution was reacted under stirring under 3.0 MPa at a temperature of 205 degree Celsius for 40 min to complete the acidolysis process. The liquid phase product was separated to provide 184 kg of levulinic acid, 75.6 kg of formic acid and 102 kg of furfural. 75.6 kg of formic acid was decomposed to provide 3.3 kg of hydrogen.

The furfural was hydrogenated on a 30% CuO-20% $Cr_2O_3$-50% $SiO_2$ precipitation type catalyst, with a reaction pressure of 2.0 MPa, a reaction temperature of 180 degree Celsius, a molar ratio of hydrogen/furfural of 10, and a space velocity of furfural of 0.5 $h^{-1}$, resulting in a conversion of furfural of 99%, and a selectivity to 2-methyl tetrahydrofuran of 92.1%. Through hydrogenation reaction, 102 kg of furfural generated 79 kg of methyl tetrahydrofuran. The hydrogen used for hydrogenations of levulinic acid and furfural was obtained from the decomposition of formic acid.

The product containing predominantly levulinic acid and the hydrogenation product of furfural predominantly containing methyl tetrahydrofuran were further converted on an aromatization catalyst. The catalyst contained 60% of ZSM-23 type zeolite (with a molar ratio of Si:Al of 25), 2.5% of $CeO_2$ and 37.5% of $Al_2O_3$. The reaction was conducted at a temperature of 480 degree Celsius under a reaction pressure of 0.8 MPa and a space velocity of 0.5 $h^{-1}$. The conversion of levulinic acid and methyl tetrahydrofuran was each 100%. The hydrocarbon product was obtained in a total amount of 124 kg, with a composition showed in I-6. The content of aromatics was 124 kg, and benzene, toluene and xylene comprised 90.0% by weight of the product. The total amount of hydrogen created was 2.4 kg, the yield of carbon as aromatics was 73.9%, and the yield of carbon as BTX aromatics was 62.5%.

TABLE I-6

| | Non-aromatic hydrocarbons | Benzene | Toluene | Ethylbenzene | P-xylene | M-xylene | O-xylene | C9 aromatics | $C_{10}^+$ aromatics |
|---|---|---|---|---|---|---|---|---|---|
| Composition/wt % | 11.5 | 8.3 | 31.8 | 4.7 | 8.3 | 17.5 | 8.9 | 7.2 | 1.8 |
| Output/KG | 14.5 | 10.4 | 39.8 | 5.9 | 10.4 | 21.9 | 11.2 | 9.0 | 2.2 |

Example I-5

The raw material was 1 t of cellulose, having a dry basis cellulose content of 98.3%. The cellulose was mixed under stirring with 3.5 t of 3.7% aqueous solution of sulfuric acid. The mixed solution was stirred under 3.0 MPa at a temperature of 205 degree Celsius for 30 min to complete the acidolysis process. The liquid phase product was separated to provide 511 kg of levulinic acid and 194 kg of formic acid. 194 kg of formic acid was decomposed to provide 8.3 kg of hydrogen.

The levulinic acid product obtained was further converted on an aromatization catalyst. The catalyst contained 60% of ZSM-5 type zeolite (with a molar ratio of Si:Al of 25), 10% of β-type zeolite (with a molar ratio of Si:Al of 60), 8% of $ZrO_2$ and 22% of $Al_2O_3$. The reaction was conducted at a temperature of 430 degree Celsius under a reaction pressure of 0.8 MPa and a space velocity of 1.0 $h^{-1}$. The conversion of levulinic acid was 100%. The hydrocarbon product was obtained in a total amount of 233 kg, with a composition showed in I-7. The content of aromatics was 216.7 kg, and benzene, toluene and xylene comprised 85.8% by weight of the product. The total amount of hydrogen created was 3.0 kg, the yield of carbon as aromatics was 87.9%, and the yield of carbon as BTX aromatics was 70.7%.

TABLE I-7

| | Non-aromatic hydrocarbons | Benzene | Toluene | Ethylbenzene | P-xylene | M-xylene | O-xylene | C9 aromatics | $C_{10}^+$ aromatics |
|---|---|---|---|---|---|---|---|---|---|
| Composition/wt % | 7.1 | 14.3 | 25.8 | 5.1 | 8.9 | 17.4 | 8.3 | 10.3 | 2.9 |
| Output/KG | 18.1 | 35.8 | 64.6 | 12.7 | 22.2 | 43.5 | 20.5 | 25.8 | 7.2 |

Example I-6

The raw material was 1 t of paddy straw, having a dry basis cellulose content of 42.5% and a dry basis hemicellulose content of 18.7%. The straw was comminuted sufficiently, 2.8 kg of tin tetrachloride was added, mixed under stirring with 5 t of 3.2% aqueous solution of sulfuric acid, and the mixed solution was reacted under stirring under 2.0 MPa at a temperature of 205 degree Celsius for 30 min to complete the acidolysis process. The liquid phase product was separated to provide 169 kg of levulinic acid, 70.3 kg of formic acid and 83.1 kg of furfural. 70.3 kg of formic acid was decomposed to provide 3 kg of hydrogen.

On a 30% CuO-10% ZnO-60% $ZrO_2$ precipitation type catalyst, with a reaction pressure of 4.0 MPa, a reaction temperature of 196 degree Celsius, a molar ratio of hydrogen/furfural of 60, and a space velocity of furfural of 0.5 $h^{-1}$, the conversion of furfural was 99%, and the selectivity to 2-methyl tetrahydrofuran was 92.1%. Through hydrogenation reaction, 83.1 kg of furfural generated 36.7 kg of methyl tetrahydrofuran. The hydrogen used for hydrogenations of levulinic acid and furfural was obtained from the decomposition of formic acid.

The product predominantly comprising methyl tetrahydrofuran and levulinic acid was further converted on an aromatization catalyst. The catalyst contained 40% of ZSM-5 type zeolite (with a molar ratio of Si:Al of 25), 20% of ZSM-11 type zeolite (with a molar ratio of Si:Al of 30) and 40% of $Al_2O_3$. The reaction was conducted at a temperature of 460 degree Celsius under a reaction pressure of 1.0 MPa and a space velocity of 3.0 $h^{-1}$. The conversion of levulinic acid was 100%, and the conversion of methyl tetrahydrofuran was 100%. The hydrocarbon product was obtained in a total amount of 101.9 kg, with a composition showed in I-8. The content of aromatics was 96.0 kg, and benzene, toluene and xylene comprised 89.2% by weight of the product. The total amount of hydrogen created was 1.5 kg, the yield of carbon as aromatics was 79.1%, and the yield of carbon as BTX aromatics was 66.5%.

and 197.6 kg of formic acid. 197.6 kg of formic acid was decomposed to provide 6.6 kg of hydrogen.

The levulinic acid was further converted on an aromatization catalyst. The catalyst contained 60% of ZSM-5 (a molar ratio of Si:Al of 38), 20% of ZSM-5 type zeolite (a molar ratio of Si:Al of 150) and 20% of $Al_2O_3$. The reaction was conducted at a temperature of 450 degree Celsius under a reaction pressure of 0.8 MPa and a space velocity of 0.5 $h^{-1}$. The conversion of levulinic acid was 100%. The hydrocarbon product was obtained in a total amount of 176.2 kg, with a composition showed in I-9. The content of aromatics was 172.7 kg, and benzene, toluene and xylene comprised 65.5% by weight of the product. The total amount of hydrogen created was 1.3 kg, and the yield of carbon as aromatics was 86.3%.

TABLE I-9

| | composition of the aromatization product | | | | | | | | |
|---|---|---|---|---|---|---|---|---|---|
| | Non-aromatic hydrocarbons | Benzene | Toluene | Ethylbenzene | P-xylene | M-xylene | O-xylene | C9 aromatics | $C_{10}^+$ aromatics |
| Composition/wt % | 2.0 | 2.2 | 21.7 | 2.7 | 8.9 | 17.7 | 11.0 | 18.4 | 15.4 |
| Output/KG | 3.5 | 3.9 | 38.2 | 4.8 | 15.7 | 31.2 | 19.4 | 32.4 | 27.1 |

Example II-1

The raw material was 1 t of bagasse, having a dry basis cellulose content of 52%. The bagasse was comminuted sufficiently, mixed under stirring with 3.5 t of 1.5% aqueous solution of hydrochloric acid, then added with 1.2 kg of iron trichloride, and the mixed solution was reacted under 1.0 MPa at a temperature of 180 degree Celsius by microwave heating for 10 min to complete the acidolysis process. The liquid phase product was separated to provide 210 kg of levulinic acid and 96.6 kg of formic acid.

Production of aromatization catalyst: 80 g of ZSM-5 having a ratio of Si:Al of 50 was mixed with 20 g of pseudo-boehmite, 3.9 g of sesbania powder was added, and mixed homogeneously. Then, 45 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide a molecular sieve catalyst.

TABLE I-8

| | composition of the aromatization product | | | | | | | | |
|---|---|---|---|---|---|---|---|---|---|
| | Non-aromatic hydrocarbons | Benzene | Toluene | Ethylbenzene | P-xylene | M-xylene | O-xylene | C9 aromatics | $C_{10}^+$ aromatics |
| Composition/wt % | 5.9 | 14.6 | 29.9 | 4.7 | 7.6 | 16.8 | 10.3 | 8.3 | 1.9 |
| Output/KG | 5.9 | 14.9 | 30.5 | 4.7 | 7.8 | 17.2 | 10.5 | 8.5 | 1.9 |

Example I-7

The raw material was 1 t of corrugated paper, having a dry basis cellulose content of 83.5%. The corrugated paper was comminuted, mixed under stirring with 5 t of 3.0% aqueous solution of sulfuric acid, then added with 13 kg of sodium chloride, and the mixed solution was reacted under stirring under 1.5 MPa at a temperature of 205 degree Celsius for 60 min to complete the acidolysis process. The liquid phase product was separated to provide 387.1 kg of levulinic acid The levulinic acid-containing stream was further converted on an aromatization catalyst. The reaction was conducted at a temperature of 450 degree Celsius under a reaction pressure of 1.0 MPa and a space velocity of 1.5 $h^{-1}$. The conversion of levulinic acid was 100%. The hydrocarbon product was obtained in a total amount of 102 kg, with a composition showed in II-1. The content of aromatics was 88.3 kg, benzene, toluene and xylene comprised 85.6% by weight of the product, and the yield of carbon as aromatics was 81.3%.

TABLE II-1 composition of the aromatization product

| | Non-aromatic hydrocarbons | Benzene | Toluene | Ethylbenzene | P-xylene | M-xylene | O-xylene | C9 aromatics | $C_{10}^+$ aromatics |
|---|---|---|---|---|---|---|---|---|---|
| Composition/wt % | 13.4 | 7.8 | 35.7 | 3.6 | 7.0 | 13.4 | 6.6 | 9.5 | 3.0 |
| Output/KG | 13.7 | 8.0 | 36.4 | 3.7 | 7.1 | 13.7 | 6.7 | 9.7 | 3.0 |

Example II-2

The raw material was 1 t of pine saw dust, having a dry basis cellulose content of 41.9%. The pine saw dust was comminuted sufficiently, mixed under stirring with 3.5 t of 2.8% aqueous solution of sulfuric acid, and the mixed solution was reacted under stirring under 3.0 MPa at a temperature of 205 degree Celsius for 40 min to complete the acidolysis process. The liquid phase product was separated to provide 184 kg of levulinic acid and 84.0 kg of formic acid.

Preparation of aromatization catalyst: 60 g of ZSM-11 having a ratio of Si:Al of 150 was mixed with 140 g of kaolin, 7.5 g of sesbania powder was added, and mixed homogeneously. Then, 92 g of an aqueous solution of 5.5 wt % nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide a molecular sieve catalyst.

The levulinic acid-containing stream was further converted on an aromatization catalyst. The reaction was conducted at a temperature of 420 degree Celsius under a reaction pressure of 1.5 MPa and a space velocity of 1.0 $h^{-1}$. The conversion of levulinic acid was 100%. The hydrocarbon product was obtained in a total amount of 76.2 kg, with a composition showed in II-2. The content of aromatics was 66.4 kg, benzene, toluene and xylene comprised 84.6% by weight of the product, and the yield of carbon as aromatics was 69.8%.

paper was comminuted sufficiently, mixed under stirring with 3.5 t of 3.5% aqueous solution of sulfuric acid, then added with 13 kg of sodium sulfite, and the mixed solution was reacted under stirring under 3.0 MPa at a temperature of 205 degree Celsius for 30 min to complete the acidolysis process. The liquid phase product was separated to provide 435.5 kg of levulinic acid and 199.4 kg of formic acid.

Production of aromatization catalyst: 300 g of MCM-22 having a ratio of Si:Al of 50 was mixed with 300 g of pseudo-boehmite, 23 g of sesbania powder was added, and mixed homogeneously. Then, 280 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 550 degree Celsius for 2 h, to provide a molecular sieve catalyst.

The levulinic acid-containing stream was further converted on an aromatization catalyst. The reaction was conducted at a temperature of 480 degree Celsius under a reaction pressure of 1.0 MPa and a space velocity of 2.0 $h^{-1}$. The conversion of levulinic acid was 100%. The hydrocarbon product was obtained in a total amount of 192.6 kg, with a composition showed in II-3. The content of aromatics was 162.2 kg, benzene, toluene and xylene comprised 82.7% by weight of the product, and the yield of carbon as aromatics was 72.3%.

TABLE II-2 composition of the aromatization product

| | Non-aromatic hydrocarbons | Benzene | Toluene | Ethylbenzene | P-xylene | M-xylene | O-xylene | C9 aromatics | $C_{10}^+$ aromatics |
|---|---|---|---|---|---|---|---|---|---|
| Composition/wt % | 12.8 | 7.5 | 34.7 | 3.9 | 7.1 | 13.8 | 6.8 | 9.0 | 4.4 |
| Output/KG | 9.8 | 5.7 | 26.4 | 3.0 | 5.4 | 10.5 | 5.2 | 6.9 | 3.3 |

Example II-3

The raw material was 1 t of municipal waste paper, having a dry basis cellulose content of 92.1%. The municipal waste

TABLE II-3 composition of the aromatization product

| | Non-aromatic hydrocarbons | Benzene | Toluene | Ethylbenzene | P-xylene | M-xylene | O-xylene | C9 aromatics | $C_{10}^+$ aromatics |
|---|---|---|---|---|---|---|---|---|---|
| Composition/wt % | 15.8 | 7.3 | 33.6 | 3.4 | 6.7 | 12.5 | 6.1 | 9.8 | 4.8 |
| Output/KG | 30.4 | 14.1 | 64.7 | 6.5 | 12.9 | 24.1 | 11.8 | 18.9 | 9.2 |

Example II-4

The raw material was 1 t of cellulose, having a dry basis cellulose content of 98.3%. The cellulose was mixed under stirring with 3.5 t of 3.7% aqueous solution of sulfuric acid. The mixed solution was stirred under 3.0 MPa at a temperature of 205 degree Celsius for 30 min to complete the acidolysis process. The liquid phase product was separated to provide 511 kg of levulinic acid and 235 kg of formic acid.

Production of aromatization catalyst: 30 g of L-type zeolite having a ratio of Si:Al of 50 was mixed with 20 g of ZSM-23 zeolite having a ratio of Si:Al of 35 and 30 g of pseudo-boehmite, 23 g of sesbania powder was added, and mixed homogeneously. Then, 36 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 550 degree Celsius for 2 h, to provide an aromatization molecular sieve catalyst.

The levulinic acid-containing stream was further converted on the aromatization catalyst. The reaction was conducted at a temperature of 450 degree Celsius under a reaction pressure of 1.5 MPa and a space velocity of 1.5 $h^{-1}$. The conversion of levulinic acid was 100%. The hydrocarbon product was obtained in a total amount of 210 kg, with a composition showed in II-4. The content of aromatics was 182.5 kg, benzene, toluene and xylene comprised 83.5% by weight of the product, and the yield of carbon as aromatics was 69.1%.

TABLE II-4

| | composition of the aromatization product | | | | | | | | |
|---|---|---|---|---|---|---|---|---|---|
| | Non-aromatic hydrocarbons | Benzene | Toluene | Ethylbenzene | P-xylene | M-xylene | O-xylene | C9 aromatics | $C_{10}^+$ aromatics |
| Composition/wt % | 13.1 | 7.5 | 34.3 | 3.7 | 7.1 | 13.2 | 6.8 | 9.6 | 4.7 |
| Output/KG | 27.5 | 15.8 | 72.0 | 7.8 | 14.9 | 27.6 | 14.3 | 20.2 | 9.9 |

Example III-1

500 g of bagasse was weighed and placed into a pressured reactor, 5000 g of water was added, and a 5 mol/L of hydrochloric acid solution having 5 wt % of water was further added. The temperature was increased to 180 degree Celsius for reaction for 1 h, cooled, and the cooled reaction liquor was filtrated to provide a filter cake and a filtrate, which filtrate was a hydrolysate of cellulose. After reaction, the reaction resultant was analyzed using a mass spectra, which showed that the main product was levulinic acid at an output of 160 g.

5 g of ZSM-5 catalyst, which had been dried at a temperature of 120 degree Celsius for 12 h to remove water, with a composition of 50 parts of ZSM-5 molecular sieve having a ratio of Si:Al of 25 and 50 parts of alumina binder, was placed into a fixed bed reactor, and activated at a temperature of 450 degree Celsius for 1 h. The reaction substrate was levulinic acid

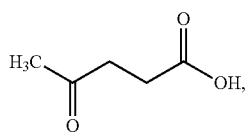

with a WHSV of 6.0 $hour^{-1}$, a hydrogen pressure of 1.0 MPa, a flow rate of 20 ml $min^{-1}$ and a temperature of 450 degree Celsius. After reaction, the reaction result was qualitatively analyzed using mass spectra, and was quantitatively analyzed using chromatogram. The conversion of substrate was 96%, the selectivity to BTX aromatics was 82%, and the yield of carbon as BTX aromatics was 78.7%.

Example III-2

600 g of corn stover was weighed and placed into a pressured reactor, 7000 g of water was added, and a 5 mol/L of sulfuric acid solution having 7 wt % of water was further added. The temperature was increased to 180 degree Celsius for reaction for 45 minutes, cooled, and the cooled reaction liquor was filtrated to provide a filter cake and a filtrate, which filtrate was a hydrolysate of cellulose. After reaction, the reaction resultant was analyzed using a mass spectra, which showed that the main product was levulinic acid at an output of 180 g.

5 g of ZSM-5 catalyst, which had been dried at a temperature of 120 degree Celsius for 12 h to remove water, with a composition of 55 parts of ZSM-5 molecular sieve having a ratio of Si:Al of 150 and 45 parts of alumina binder, was placed into a fixed bed reactor, and activated at a temperature of 450 degree Celsius for 1 h. The reaction substrate was levulinic acid, with a WHSV of 0.8 $hour^{-1}$, a hydrogen pressure of 2.0 MPa, a flow rate of 20 ml $min^{-1}$ and a temperature of 450 degree Celsius. After reaction, the reaction result was qualitatively analyzed using mass spectra, and was quantitatively analyzed using chromatogram. The conversion of substrate was 94%, the selectivity to BTX aromatics was 93%, and the yield of carbon as BTX aromatics was 87.4%.

Example III-3

500 g of glucose was weighed and placed into a pressured reactor, 6000 g of water was added, and a 5 mol/L of sulfuric acid solution having 3 wt % of water was further added. The temperature was increased to 180 degree Celsius for reaction for 0.5 h, cooled, and the cooled reaction liquor was filtrated, from which the filtrate obtained was analyzed for reaction result using a mass spectra, which showed that the main product was levulinic acid at an output of 140 g.

5 g of ZSM-5 catalyst, which had been dried at a temperature of 120 degree Celsius for 12 h to remove water, with a composition of 60 parts of ZSM-5 molecular sieve having a ratio of Si:Al of 500 and 40 parts of alumina binder, was placed into a fixed bed reactor, and activated at a temperature of 450 degree Celsius for 1 h. The reaction substrate was levulinic

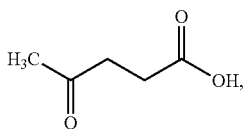

with a WHSV of 1.0 hour$^{-1}$, a hydrogen pressure of 3.0 MPa, a flow rate of 50 ml min$^{-1}$ and a temperature of 400 degree Celsius. After reaction, the reaction result was qualitatively analyzed using mass spectra, and was quantitatively analyzed using chromatogram. The conversion of substrate was 91%, the selectivity to BTX aromatics was 86%, and the yield of carbon as BTX aromatics was 78.3%.

Example III-4

5 g of beta catalyst, which had been dried at a temperature of 120 degree Celsius for 12 h to remove water, with a composition of 50 parts of beta molecular sieve having a ratio of Si:Al of 30 and 50 parts of alumina binder, was placed into a fixed bed reactor, and activated at a temperature of 450 degree Celsius for 1 h. The reaction substrate was levulinic acid

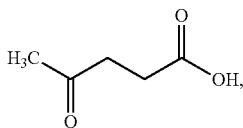

with a WHSV of 1.0 hour$^{-1}$, a hydrogen pressure of 1.0 MPa, a flow rate of 20 ml min$^{-1}$ and a temperature of 450 degree Celsius. After reaction, the reaction result was qualitatively analyzed using mass spectra, and was quantitatively analyzed using chromatogram. The conversion of substrate was 89%, the selectivity to BTX aromatics was 78%, and the yield of carbon as BTX aromatics was 69.4%.

Example III-5

5 g of beta catalyst, which had been dried at a temperature of 120 degree Celsius for 12 h to remove water, with a composition of 40 parts of beta molecular sieve having a ratio of Si:Al of 100 and 60 parts of alumina binder, was placed into a fixed bed reactor, and activated at a temperature of 450 degree Celsius for 1 h. The reaction substrate was levulinic acid

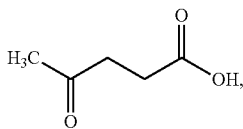

with a WHSV of 2.0 hour$^{-1}$, a hydrogen pressure of 1.0 MPa, a flow rate of 50 ml min$^{-1}$ and a temperature of 450 degree Celsius. After reaction, the reaction result was qualitatively analyzed using mass spectra, and was quantitatively analyzed using chromatogram. The conversion of substrate was 85%, the selectivity to BTX aromatics was 71%, and the yield of carbon as BTX aromatics was 60.4%.

Example III-6

600 g of straw stover was weighed and placed into a pressured reactor, 7000 g of water was added, and a 5 mol/L of sulfuric acid solution having 7 wt % of water was further added. The temperature was increased to 210 degree Celsius for reaction for 30 minutes, cooled, and the cooled reaction liquor was filtrated to provide a filter cake and a filtrate, which filtrate was a hydrolysate of cellulose. After reaction, the reaction resultant was analyzed using a mass spectra, which showed that the main product was levulinic acid at an output of 228 g.

5 g of MCM-41 catalyst, which had been dried at a temperature of 120 degree Celsius for 12 h to remove water, with a composition of 50 parts of MCM-41 molecular sieve having a ratio of Si:Al of 50 and 50 parts of alumina binder, was placed into a fixed bed reactor, and activated at a temperature of 450 degree Celsius for 1 h. The reaction substrate was levulinic acid

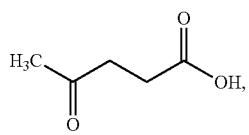

with a WHSV of 1.0 hour$^{-1}$, a hydrogen pressure of 3.0 MPa, a flow rate of 30 ml min$^{-1}$ and a temperature of 450 degree Celsius. After reaction, the reaction result was qualitatively analyzed using mass spectra, and was quantitatively analyzed using chromatogram. The conversion of substrate was 89%, the selectivity to BTX aromatics was 76%, and the yield of carbon as BTX aromatics was 67.6%.

Example III-7

5 g of MCM-22 catalyst, which had been dried at a temperature of 120 degree Celsius for 12 h to remove water, with a composition of 50 parts of MCM-22 molecular sieve having a ratio of Si:Al of 70 and 50 parts of alumina binder, was placed into a fixed bed reactor, and activated at a temperature of 450 degree Celsius for 1 h. The reaction substrate was levulinic acid

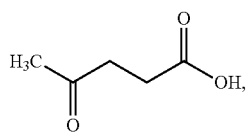

with a WHSV of 1.0 hour$^{-1}$, a hydrogen pressure of 1.0 MPa, a flow rate of 20 ml min$^{-1}$ and a temperature of 450 degree Celsius. After reaction, the reaction result was qualitatively analyzed using mass spectra, and was quantitatively analyzed using chromatogram. The conversion of substrate was 91%, the selectivity to BTX aromatics was 83%, and the yield of carbon as BTX aromatics was 75.5%.

Example III-8

300 g of wood was weighed and placed into a pressured reactor, 4000 g of water was added, and a 5 mol/L of sulfuric acid solution having 7 wt % of water was further added. The temperature was increased to 200 degree Celsius for reaction for 30 minutes, cooled, and the cooled reaction liquor was filtrated to provide a filter cake and a filtrate, which filtrate was a hydrolysate of cellulose. After reaction, the reaction resultant was analyzed using a mass spectra, which showed that the main product was levulinic acid at an output of 105 g.

5 g of MCM-41 catalyst, which had been dried at a temperature of 120 degree Celsius for 12 h to remove water, with a composition of 50 parts of MCM-41 molecular sieve having a ratio of Si:Al of 150 and 50 parts of alumina binder, was placed into a fixed bed reactor, and activated at a temperature of 450 degree Celsius for 1 h. The reaction substrate was levulinic acid

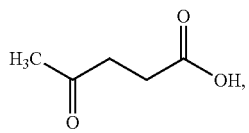

with a WHSV of 1.0 hour$^{-1}$, a hydrogen pressure of 1.0 MPa, a flow rate of 20 ml min$^{-1}$ and a temperature of 400 degree Celsius. After reaction, the reaction result was qualitatively analyzed using mass spectra, and was quantitatively analyzed using chromatogram. The conversion of substrate was 86%, the selectivity to BTX aromatics was 76%, and the yield of carbon as BTX aromatics was 65.4%.

TABLE III-1

| Example | Substrate | Catalyst | Ratio of Si:Al | Conversion/% | Selectivity to BTX/% |
|---|---|---|---|---|---|
| 1 | Levulinic acid | ZSM-5 | 25 | 96 | 82 |
| 2 | Levulinic acid | ZSM-5 | 150 | 94 | 93 |
| 3 | Levulinic acid | ZSM-5 | 500 | 91 | 86 |
| 4 | Levulinic acid | beta | 30 | 89 | 78 |
| 5 | Levulinic acid | beta | 100 | 85 | 71 |
| 6 | Levulinic acid | MCM-41 | 50 | 89 | 76 |
| 7 | Levulinic acid | MCM-22 | 70 | 91 | 83 |
| 8 | Levulinic acid | MCM-41 | 150 | 86 | 76 |

Example IV-1

600 g of straw stover was weighed and placed into a pressured reactor, 7000 g of water was added, and a 5 mol/L of sulfuric acid solution having 7 wt % of water was further added. The temperature was increased to 210 degree Celsius for reaction for 30 minutes, cooled, and the cooled reaction liquor was filtrated to provide a filter cake and a filtrate, which filtrate was a hydrolysate of cellulose. After reaction, the reaction resultant was analyzed using a mass spectra, which showed that the main product was levulinic acid at an output of 228 g.

5 g of SO$_4^{2-}$/ZrO$_2$ catalyst, which had been dried at a temperature of 120 degree Celsius for 12 h to remove water, was weighed and placed into a fixed bed reactor. The reaction substrate was levulinic acid

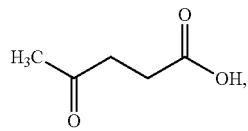

with a WHSV of 0.3 hour$^{-1}$, a hydrogen pressure of 1.0 MPa, a flow rate of 50 ml min$^{-1}$ and a temperature of 400 degree Celsius. After reaction, the reaction result was qualitatively analyzed using mass spectra, and was quantitatively analyzed using chromatogram. The conversion of substrate was 83%, the selectivity to BTX aromatics was 87%, and the yield of carbon as BTX aromatics was 72.2%.

Example IV-2

5 g of S$_2$O$_8^{2-}$/ZrO$_2$ catalyst, which had been dried at a temperature of 120 degree Celsius for 12 h to remove water, was weighed and placed into a fixed bed reactor. The reaction substrate was levulinic acid, with a WHSV of 1.0 hour$^{-1}$, a hydrogen pressure of 1.0 MPa, a flow rate of 20 ml min$^{-1}$ and a temperature of 450 degree Celsius. After reaction, the reaction result was qualitatively analyzed using mass spectra, and was quantitatively analyzed using chromatogram. The conversion of substrate was 98%, the selectivity to BTX aromatics was 93%, and the yield of carbon as BTX aromatics was 91.1%.

Example IV-3

5 g of SO$_4^{2-}$/TiO$_2$ catalyst, which had been dried at a temperature of 120 degree Celsius for 12 h to remove water, was weighed and placed into a fixed bed reactor. The reaction substrate was levulinic acid, with a WHSV of 3.0 hour$^{-1}$, a hydrogen pressure of 1.0 MPa, a flow rate of 20 ml min$^{-1}$ and a temperature of 400 degree Celsius. After reaction, the reaction result was qualitatively analyzed using mass spectra, and was quantitatively analyzed using chromatogram. The conversion of substrate was 88%, the selectivity to BTX aromatics was 81%, and the yield of carbon as BTX aromatics was 71.3%.

Example IV-4

300 g of wood was weighed and placed into a pressured reactor, 4000 g of water was added, and a 5 mol/L of sulfuric acid solution having 7 wt % of water was further added. The temperature was increased to 200 degree Celsius for reaction for 30 minutes, cooled, and the cooled reaction liquor was filtrated to provide a filter cake and a filtrate, which filtrate was a hydrolysate of cellulose. After reaction, the reaction resultant was analyzed using a mass spectra, which showed that the main product was levulinic acid at an output of 105 g.

5 g of SO$_4^{2-}$/ZrO$_2$—Fe$_3$O$_4$ catalyst, which had been dried at a temperature of 120 degree Celsius for 12 h to remove water, was placed into a fixed bed reactor. The reaction substrate was levulinic acid, with a WHSV of 5.0 hour$^{-1}$, a hydrogen pressure of 1.0 MPa, a flow rate of 20 ml min$^{-1}$ and a temperature of 500 degree Celsius. After reaction, the reaction result was qualitatively analyzed using mass spectra, and was quantitatively analyzed using chromatogram. The conversion of substrate was 82%, the selectivity to BTX aromatics was 78%, and the yield of carbon as BTX aromatics was 64.0%.

Example IV-5

5 g of $Pt/SO_4^{2-}/TiO_2$ catalyst, which had been dried at a temperature of 120 degree Celsius for 12 h to remove water, was weighed and placed into a fixed bed reactor. The reaction substrate was levulinic acid, with a WHSV of 2.0 hour$^{-1}$, a hydrogen pressure of 3.0 MPa, a flow rate of 20 ml min$^{-1}$ and a temperature of 450 degree Celsius. After reaction, the reaction result was qualitatively analyzed using mass spectra, and was quantitatively analyzed using chromatogram. The conversion of substrate was 89%, the selectivity to BTX aromatics was 81%, and the yield of carbon as BTX aromatics was 72.1%.

Example IV-6

5 g of $SO_4^{2-}/TiO_2$—$ZrO_2$ catalyst, which had been dried at a temperature of 120 degree Celsius for 12 h to remove water, was weighed and placed into a fixed bed reactor. The reaction substrate was levulinic acid, with a WHSV of 0.8 hour$^{-1}$, a hydrogen pressure of 1.0 MPa, a flow rate of 40 ml min$^{-1}$ and a temperature of 400 degree Celsius. After reaction, the reaction result was qualitatively analyzed using mass spectra, and was quantitatively analyzed using chromatogram. The conversion of substrate was 87%, the selectivity to BTX aromatics was 81%, and the yield of carbon as BTX aromatics was 70.5%.

Example IV-7

5 g of $SO_4^{2-}/ZrO_2$—$WO_3$ catalyst, which had been dried at a temperature of 120 degree Celsius for 12 h to remove water, was weighed and placed into a fixed bed reactor. The reaction substrate was levulinic acid, with a WHSV of 1.0 hour$^{-1}$, a hydrogen pressure of 1.0 MPa, a flow rate of 20 ml min$^{-1}$ and a temperature of 380 degree Celsius. After reaction, the reaction result was qualitatively analyzed using mass spectra, and was quantitatively analyzed using chromatogram. The conversion of substrate was 92%, the selectivity to BTX aromatics was 90%, and the yield of carbon as BTX aromatics was 82.8%.

Example IV-8

5 g of $SO_4^{2-}/ZrO_2$—$Fe_2O_3$—$Cr_2O_3$ catalyst, which had been dried at a temperature of 120 degree Celsius for 12 h to remove water, was weighed and placed into a fixed bed reactor. The reaction substrate was levulinic acid, with a WHSV of 1.0 hour$^{-1}$, a hydrogen pressure of 1.0 MPa, a flow rate of 20 ml min$^{-1}$ and a temperature of 380 degree Celsius. After reaction, the reaction result was qualitatively analyzed using mass spectra, and was quantitatively analyzed using chromatogram. The conversion of substrate was 94%, the selectivity to BTX aromatics was 87%, and the yield of carbon as BTX aromatics was 81.8%.

TABLE IV-1

| Example | Substrate | Catalyst | Conversion/% | Selectivity to BTX/% |
|---|---|---|---|---|
| 1 | Levulinic acid | $SO_4^{2-}/ZrO_2$ | 83 | 87 |
| 2 | Levulinic acid | $S_2O_8^{2-}/ZrO_2$ | 98 | 93 |
| 3 | Levulinic acid | $SO_4^{2-}/TiO_2$ | 88 | 81 |
| 4 | Levulinic acid | $SO_4^{2-}/ZrO_2$—$Fe_3O_4$ | 82 | 78 |
| 5 | Levulinic acid | $Pt/SO_4^{2-}/TiO_2$ | 89 | 81 |
| 6 | Levulinic acid | $SO_4^{2-}/TiO_2$—$ZrO_2$ | 87 | 81 |
| 7 | Levulinic acid | $SO_4^{2-}/ZrO_2$—$WO_3$ | 92 | 90 |
| 8 | Levulinic acid | $SO_4^{2-}/ZrO_2$—$Fe_2O_3$—$Cr_2O_3$ | 94 | 87 |

Example V-1

600 g of corn stover was weighed and placed into a pressured reactor, 7000 g of water was added, and a 5 mol/L of sulfuric acid solution having 7 wt % of water was further added. The temperature was increased to 180 degree Celsius for reaction for 45 minutes, cooled, and the cooled reaction liquor was filtrated to provide a filter cake and a filtrate, which filtrate was a hydrolysate of cellulose. After reaction, the reaction resultant was analyzed using a mass spectra, which showed that the main product was levulinic acid at an output of 180 g.

5 g of $WO_3/ZrO_2$ catalyst, which had been dried at a temperature of 120 degree Celsius for 12 h to remove water, having a proportion of metal oxide of 5/95, was weighed and placed into a fixed bed reactor. The reaction substrate was levulinic acid

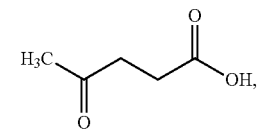

with a WHSV of 1.0 hour$^{-1}$, a hydrogen pressure of 1.0 MPa, a flow rate of 50 ml min$^{-1}$ and a temperature of 450 degree Celsius. After reaction, the reaction result was qualitatively analyzed using mass spectra, and was quantitatively analyzed using chromatogram. The conversion of substrate was 93%, the selectivity to BTX aromatics was 84%, and the yield of carbon as BTX aromatics was 78.1%.

Example V-2

600 g of straw stover was weighed and placed into a pressured reactor, 5000 g of water was added, and a 5 mol/L of sulphuric acid solution having 7 wt % of water was further added. The temperature was increased to 210 degree Celsius for reaction for 30 minutes, cooled, and the cooled reaction liquor was filtrated to provide a filter cake and a filtrate, which filtrate was a hydrolysate of cellulose. After reaction, the reaction resultant was analyzed using a mass spectra, which showed that the main product was levulinic acid at an output of 228 g.

5 g of $WO_3/ZrO_2$ catalyst, which had been dried at a temperature of 120 degree Celsius for 12 h to remove water, having a proportion of metal oxide of 20/80, was weighed and placed into a fixed bed reactor. The reaction substrate was levulinic acid

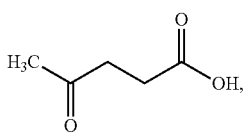

with a WHSV of 2.5 hour$^{-1}$, a hydrogen pressure of 2.0 MPa, a flow rate of 20 ml min$^{-1}$ and a temperature of 380 degree Celsius. After reaction, the reaction result was qualitatively analyzed using mass spectra, and was quantitatively analyzed using chromatogram. The conversion of substrate was 97%, the selectivity to BTX aromatics was 86%, and the yield of carbon as BTX aromatics was 83.4%.

Example V-3

5 g of MoO$_3$/ZrO$_2$ catalyst, which had been dried at a temperature of 120 degree Celsius for 12 h to remove water, having a proportion of metal oxide of 10/90, was weighed and placed into a fixed bed reactor. The reaction substrate was levulinic acid

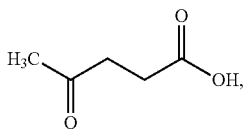

with a WHSV of 3.0 hour$^{-1}$, a hydrogen pressure of 1.0 MPa, a flow rate of 20 ml min$^{-1}$ and a temperature of 480 degree Celsius. After reaction, the reaction result was qualitatively analyzed using mass spectra, and was quantitatively analyzed using chromatogram. The conversion of substrate was 91%, the selectivity to BTX aromatics was 81%, and the yield of carbon as BTX aromatics was 73.7%.

Example V-4

300 g of wood was weighed and placed into a pressured reactor, 4000 g of water was added, and a 5 mol/L of sulphuric acid solution having 7 wt % of water was further added. The temperature was increased to 200 degree Celsius for reaction for 30 minutes, cooled, and the cooled reaction liquor was filtrated to provide a filter cake and a filtrate, which filtrate was a hydrolysate of cellulose. After reaction, the reaction resultant was analyzed using a mass spectra, which showed that the main product was levulinic acid at an output of 105 g.

5 g of CeO$_2$/ZrO$_2$ catalyst, which had been dried at a temperature of 120 degree Celsius for 12 h to remove water, having a proportion of metal oxide of 10/90, was weighed and placed into a fixed bed reactor. The reaction substrate was levulinic acid

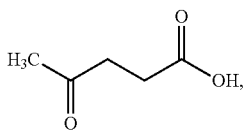

with a WHSV of 3.0 hour$^{-1}$, a hydrogen pressure of 1.0 MPa, a flow rate of 20 ml min$^{-1}$ and a temperature of 450 degree Celsius. After reaction, the reaction result was qualitatively analyzed using mass spectra, and was quantitatively analyzed using chromatogram. The conversion of substrate was 86%, the selectivity to BTX aromatics was 80%, and the yield of carbon as BTX aromatics was 68.8%.

TABLE V-1

| Example | Substrate | Catalyst | Metal oxide proportion | Conversion/% | Selectivity to BTX/% |
| --- | --- | --- | --- | --- | --- |
| 1 | Levulinic acid | WO$_3$/ZrO$_2$ | 5/95 | 93 | 84 |
| 2 | Levulinic acid | WO$_3$/ZrO$_2$ | 20/80 | 97 | 86 |
| 3 | Levulinic acid | MoO$_3$/ZrO$_2$ | 10/90 | 91 | 81 |
| 4 | Levulinic acid | CeO$_2$/ZrO$_2$ | 10/90 | 86 | 80 |

Example VI-1

600 g of corn stover was weighed and placed into a pressured reactor, 6000 g of water was added, and a 5 mol/L of sulphuric acid solution having 7 wt % of water was further added. The temperature was increased to 180 degree Celsius for reaction for 45 minutes, cooled, and the cooled reaction liquor was filtrated to provide a filter cake and a filtrate, which filtrate was a hydrolysate of cellulose. After reaction, the reaction resultant was analyzed using a mass spectra, which showed that the main product was levulinic acid at an output of 180 g.

35 g of ZSM-5 having a ratio of Si:Al of 25 was mixed with 35 g of an auxiliary of γ-alumina, 2.7 g of sesbania powder was added, and mixed homogeneously. Then, 48 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide a molecular sieve catalyst C1.

The catalyst was evaluated for activity on a fixed bed, under reaction conditions of: 3 g of catalyst, the reaction substrate being levulinic acid, a WHSV of 1.0 hour$^{-1}$, a hydrogen pressure of 1.0 MPa, a flow rate of 50 ml min$^{-1}$, and a temperature of 400 degree Celsius. After reaction, the conversion of the reaction substrate was 95%, the selectivity to BTX aromatics was 87%, and the yield of carbon as BTX aromatics was 83%.

Example VI-2

35 g of ZSM-5 having a ratio of Si:Al of 50 was mixed with 35 g of pseudo-boehmite, 2.7 g of sesbania powder was added, and mixed homogeneously. Then, 48 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide a molecular sieve catalyst C2.

The catalyst was evaluated for activity on a fixed bed, under reaction conditions of: 3 g of catalyst, the reaction substrate being levulinic acid, a WHSV of 3.0 hour$^{-1}$, a hydrogen pressure of 1.0 MPa, a flow rate of 50 ml min$^{-1}$, and a temperature of 450 degree Celsius. After reaction, the conversion of the reaction substrate was 96%, the selectivity to BTX aromatics was 86%, and the yield of carbon as BTX aromatics was 83%.

Example VI-3

35 g of ZSM-5 having a ratio of Si:Al of 150 was mixed with 35 g of pseudo-boehmite, 2.7 g of sesbania powder was added, and mixed homogeneously. Then, 48 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide a molecular sieve catalyst C3.

The catalyst was evaluated for activity on a fixed bed, under reaction conditions of: 3 g of catalyst, the reaction substrate being levulinic acid, a WHSV of 2.5 hour$^{-1}$, a hydrogen pressure of 4.0 MPa, a flow rate of 50 ml min$^{-1}$, and a temperature of 550 degree Celsius. After reaction, the conversion of the reaction substrate was 99%, the selectivity to BTX aromatics was 89%, and the yield of carbon as BTX aromatics was 88%.

Example VI-4

80 g of ZSM-5 having a ratio of Si:Al of 500 was mixed with 20 g of pseudo-boehmite, 3.9 g of sesbania powder was added, and mixed homogeneously. Then, 68.6 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide a molecular sieve catalyst C4.

The catalyst was evaluated for activity on a fixed bed, under reaction conditions of: 3 g of catalyst, the reaction substrate being levulinic acid, a WHSV of 5.0 hour$^{-1}$, a hydrogen pressure of 1.0 MPa, a flow rate of 30 ml min$^{-1}$, and a temperature of 380 degree Celsius. After reaction, the conversion of the reaction substrate was 96%, the selectivity to BTX aromatics was 83%, and the yield of carbon as BTX aromatics was 80%.

Example VI-5

80 g of ZSM-38 having a ratio of Si:Al of 150 was mixed with 20 g of silica sol, 3.9 g of sesbania powder was added, and mixed homogeneously. Then, 68.6 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide a molecular sieve catalyst C5.

The catalyst was evaluated for activity on a fixed bed, under reaction conditions of: 3 g of catalyst, the reaction substrate being methyl levulinate, a WHSV of 0.3 hour$^{-1}$, a hydrogen pressure of 3.0 MPa, a flow rate of 50 ml min$^{-1}$, and a temperature of 450 degree Celsius. After reaction, the conversion of the reaction substrate was 99%, the selectivity to BTX aromatics was 94%, and the yield of carbon as BTX aromatics was 93%.

Example VI-6

80 g of ZSM-11 having a ratio of Si:Al of 150 was mixed with 20 g of kaolin, 3.9 g of sodium carboxymethylcellulose was added, and mixed homogeneously. Then, 68.6 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide a molecular sieve catalyst C6.

The catalyst was evaluated for activity on a fixed bed, under reaction conditions of: 3 g of catalyst, the reaction substrate being methyl levulinate, a WHSV of 4.0 hour$^{-1}$, a hydrogen pressure of 1.0 MPa, a flow rate of 50 ml min$^{-1}$, and a temperature of 480 degree Celsius. After reaction, the conversion of the reaction substrate was 96%, the selectivity to BTX aromatics was 86%, and the yield of carbon as BTX aromatics was 83%.

Example VI-7

70 g of ZSM-11 having a ratio of Si:Al of 100 was mixed with 30 g of kaolin, 3.9 g of sesbania powder was added, and mixed homogeneously. Then, 68.6 g of an aqueous solution of phosphoric acid comprising 5.5 wt % of phosphoric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide a molecular sieve catalyst C6.

The catalyst was evaluated for activity on a fixed bed, under reaction conditions of: 3 g of catalyst, the reaction substrate being ethyl levulinate, a WHSV of 2.0 hour$^{-1}$, a hydrogen pressure of 1.0 MPa, a flow rate of 50 ml min$^{-1}$, and a temperature of 450 degree Celsius. After reaction, the conversion of the reaction substrate was 92%, the selectivity to BTX aromatics was 83%, and the yield of carbon as BTX aromatics was 76%.

Example VI-8

50 g of ZSM-23 having a ratio of Si:Al of 100 was mixed with 50 g of alumina, 3.9 g of sesbania powder was added, and mixed homogeneously. Then, 68.6 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide a molecular sieve catalyst C6.

The catalyst was evaluated for activity on a fixed bed, under reaction conditions of: 3 g of catalyst, the reaction substrate being ethyl levulinate, a WHSV of 4.0 hour$^{-1}$, a hydrogen pressure of 1.0 MPa, a flow rate of 50 ml min$^{-1}$, and a temperature of 450 degree Celsius. After reaction, the conversion of the reaction substrate was 99%, the selectivity to BTX aromatics was 81%, and the yield of carbon as BTX aromatics was 80%.

Example VI-9

35 g of ZSM-5 having a ratio of Si:Al of 100 was mixed with 35 g of an auxiliary of γ-alumina, 2.7 g of sesbania powder was added, and mixed homogeneously. Then, 48 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide a molecular sieve catalyst C9.

The catalyst was evaluated for activity on a fixed bed, under reaction conditions of: 3 g of catalyst, the reaction substrate being butyl levulinate, a WHSV of 5.0 hour$^{-1}$, a hydrogen pressure of 1.0 MPa, a flow rate of 50 ml min$^{-1}$, and a temperature of 350 degree Celsius. After reaction, the conversion of the reaction substrate was 89%, the selectivity to BTX aromatics was 83%, and the yield of carbon as BTX aromatics was 74%.

Example VI-10

35 g of Y having a ratio of Si:Al of 6 was mixed with 35 g of an auxiliary of γ-alumina, 2.7 g of sodium carboxymethylcellulose was added, and mixed homogeneously. Then, 48 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide a molecular sieve catalyst C10.

The catalyst was evaluated for activity on a fixed bed, under reaction conditions of: 3 g of catalyst, the reaction substrate being butyl levulinate, a WHSV of 1.0 hour$^{-1}$, a hydrogen pressure of 1.0 MPa, a flow rate of 50 ml min$^{-1}$, and a temperature of 430 degree Celsius. After reaction, the conversion of the reaction substrate was 81%, the selectivity to BTX aromatics was 87%, and the yield of carbon as BTX aromatics was 70%.

Example VI-11

60 g of Y having a ratio of Si:Al of 8 was mixed with 40 g of an auxiliary of γ-alumina, 3.9 g of sesbania powder was added, and mixed homogeneously. Then, 68.6 g of an aqueous solution of phosphoric acid comprising 5.5 wt % of phosphoric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide a molecular sieve catalyst C11.

The catalyst was evaluated for activity on a fixed bed, under reaction conditions of: 3 g of catalyst, the reaction substrate being methyl levulinate, a WHSV of 0.3 hour$^{-1}$, a hydrogen pressure of 2.0 MPa, a flow rate of 50 ml min$^{-1}$, and a temperature of 450 degree Celsius. After reaction, the conversion of the reaction substrate was 93%, the selectivity to BTX aromatics was 78%, and the yield of carbon as BTX aromatics was 73%.

Example VI-12

70 g of Y having a ratio of Si:Al of 8 was mixed with 30 g of pseudo-boehmite, 3.9 g of sesbania powder was added, and mixed homogeneously. Then, 68.6 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide a molecular sieve catalyst C12.

The catalyst was evaluated for activity on a fixed bed, under reaction conditions of: 3 g of catalyst, the reaction substrate being methyl levulinate, a WHSV of 1.0 hour$^{-1}$, a hydrogen pressure of 1.0 MPa, a flow rate of 50 ml min$^{-1}$, and a temperature of 400 degree Celsius. After reaction, the conversion of the reaction substrate was 94%, the selectivity to BTX aromatics was 79%, and the yield of carbon as BTX aromatics was 74%.

Example VI-13

80 g of Y having a ratio of Si:Al of 8 was mixed with 20 g of pseudo-boehmite, 3.9 g of sesbania powder was added, and mixed homogeneously. Then, 68.6 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide a molecular sieve catalyst C13.

The catalyst was evaluated for activity on a fixed bed, under reaction conditions of: 3 g of catalyst, the reaction substrate being methyl levulinate, a WHSV of 1.0 hour$^{-1}$, a hydrogen pressure of 1.0 MPa, a flow rate of 50 ml min$^{-1}$, and a temperature of 470 degree Celsius. After reaction, the conversion of the reaction substrate was 86%, the selectivity to BTX aromatics was 87%, and the yield of carbon as BTX aromatics was 75%.

Example VI-14

50 g of beta having a ratio of Si:Al of 30 was mixed with 50 g of pseudo-boehmite, 3.9 g of sesbania powder was added, and mixed homogeneously. Then, 68.6 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide a molecular sieve catalyst C15.

The catalyst was evaluated for activity on a fixed bed, under reaction conditions of: 3 g of catalyst, the reaction substrate being methyl levulinate, a WHSV of 1.0 hour$^{-1}$, a hydrogen pressure of 1.0 MPa, a flow rate of 50 ml min$^{-1}$, and a temperature of 430 degree Celsius. After reaction, the conversion of the reaction substrate was 91%, the selectivity to BTX aromatics was 82%, and the yield of carbon as BTX aromatics was 75%.

Example VI-15

60 g of beta having a ratio of Si:Al of 50 was mixed with 40 g of pseudo-boehmite, 3.9 g of sesbania powder was added, and mixed homogeneously. Then, 68.6 g of an aqueous solution of nitric acid comprising 5.5 wt % of acetic acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide a molecular sieve catalyst C15.

The catalyst was evaluated for activity on a fixed bed, under reaction conditions of: 3 g of catalyst, the reaction substrate being butyl levulinate, a WHSV of 1.0 hour$^{-1}$, a hydrogen pressure of 1.0 MPa, a flow rate of 50 ml min$^{-1}$, and a temperature of 400 degree Celsius. After reaction, the conversion of the reaction substrate was 88%, the selectivity to BTX aromatics was 77%, and the yield of carbon as BTX aromatics was 68%.

Example VI-16

70 g of beta having a ratio of Si:Al of 100 was mixed with 30 g of pseudo-boehmite, 3.9 g of sesbania powder was added, and mixed homogeneously. Then, 68.6 g of an aqueous solution of nitric acid comprising 5.5 wt % of acetic acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide a molecular sieve catalyst C16.

The catalyst was evaluated for activity on a fixed bed, under reaction conditions of: 3 g of catalyst, the reaction substrate being butyl levulinate, a WHSV of 1.0 hour$^{-1}$, a hydrogen pressure of 1.0 MPa, a flow rate of 50 ml min$^{-1}$, and a temperature of 400 degree Celsius. After reaction, the conversion of the reaction substrate was 84%, the selectivity to BTX aromatics was 88%, and the yield of carbon as BTX aromatics was 74%.

Example VI-17

50 g of MCM-41 having a ratio of Si:Al of 20 was mixed with 50 g of pseudo-boehmite, 3.9 g of sesbania powder was added, and mixed homogeneously. Then, 68.6 g of an aqueous solution of acetic acid comprising 5.5 wt % of acetic acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide a molecular sieve catalyst C17.

The catalyst was evaluated for activity on a fixed bed, under reaction conditions of: 3 g of catalyst, the reaction substrate being butyl levulinate, a WHSV of 1.0 hour$^{-1}$, a hydrogen pressure of 1.0 MPa, a flow rate of 50 ml min$^{-1}$, and a temperature of 400 degree Celsius. After reaction, the conversion of the reaction substrate was 81%, the selectivity to BTX aromatics was 82%, and the yield of carbon as BTX aromatics was 66%.

Example VI-18

50 g of MCM-22 having a ratio of Si:Al of 50 was mixed with 50 g of pseudo-boehmite, 3.9 g of sesbania powder was added, and mixed homogeneously. Then, 68.6 g of an aqueous solution of acetic acid comprising 5.5 wt % of acetic acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide a molecular sieve catalyst C18.

The catalyst was evaluated for activity on a fixed bed, under reaction conditions of: 3 g of catalyst, the reaction substrate being butyl levulinate, a WHSV of 0.3 hour$^{-1}$, a hydrogen pressure of 0.3 MPa, a flow rate of 50 ml min$^{-1}$, and a temperature of 480 degree Celsius. After reaction, the conversion of the reaction substrate was 83%, the selectivity to BTX aromatics was 89%, and the yield of carbon as BTX aromatics was 74%.

Comparative Example VI-1

Comparative example VI-1 was practiced to illustrate the synthesis of a catalyst comprising 5A type as the main active component, the preparation of catalyst and the properties thereof for aromatization of levulic acid. The specific reactants formulation and the experimental method were provided as follows:

35 g of 5A molecular sieve having a ratio of Si:Al of 2 was mixed with 35 g of an auxiliary of γ-alumina, 2.7 g of sesbania powder was added, and mixed homogeneously. Then, 48 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide a molecular sieve catalyst C5A.

The catalyst was evaluated for activity on a fixed bed, under reaction conditions of: 3 g of catalyst, the reaction substrate being levulinic acid, a WHSV of 1.0 hour$^{-1}$, a hydrogen pressure of 1.0 MPa, a flow rate of 50 ml min$^{-1}$, a temperature of 400 degree Celsius. After reaction, calculation of the reaction result showed that the conversion of the reaction substrate was 35%, the selectivity to BTX aromatics was 17%, and the yield of carbon as BTX aromatics was 6%.

TABLE VI-1

| Cat | Molecular sieve | Ratio of Si:Al | Binder | Molecular sieve/binder proportion | Substrate | Conversion % | BTX selectivity % |
| --- | --- | --- | --- | --- | --- | --- | --- |
| C1 | ZSM-5 | 25 | Alumina | 50/50 | Levulinic acid | 95 | 87 |
| C2 | ZSM-5 | 50 | Pseudo-boehmite | 50/50 | Levulinic acid | 96 | 86 |
| C3 | ZSM-5 | 150 | Pseudo-boehmite | 50/50 | Levulinic acid | 99 | 89 |
| C4 | ZSM-5 | 500 | Pseudo-boehmite | 80/20 | Levulinic acid | 96 | 83 |
| C5 | ZSM-38 | 150 | Silica sol | 80/20 | Methyl levulinate | 99 | 94 |
| C6 | ZSM-11 | 150 | Kaolin | 80/20 | Methyl levulinate | 96 | 86 |
| C7 | ZSM-11 | 100 | Kaolin | 70/30 | Ethyl levulinate | 92 | 83 |
| C8 | ZSM-23 | 100 | Alumina | 50/50 | Ethyl levulinate | 99 | 81 |
| C9 | ZSM-5 | 100 | Alumina | 50/50 | Butyl levulinate | 89 | 83 |
| C10 | Y | 6 | Alumina | 50/50 | Butyl levulinate | 81 | 87 |
| C11 | Y | 8 | Alumina | 60/40 | Methyl levulinate | 93 | 78 |
| C12 | Y | 8 | Pseudo-boehmite | 70/30 | Methyl levulinate | 94 | 79 |
| C13 | Y | 8 | Pseudo-boehmite | 80/20 | Methyl levulinate | 86 | 87 |
| C14 | beta | 30 | Alumina | 50/50 | Methyl levulinate | 91 | 82 |

TABLE VI-1-continued

| Cat | Molecular sieve | Ratio of Si:Al | Binder | Molecular sieve/binder proportion | Substrate | Conversion % | BTX selectivity % |
|---|---|---|---|---|---|---|---|
| C15 | beta | 50 | Pseudo-boehmite | 60/40 | Butyl levulinate | 88 | 77 |
| C16 | beta | 100 | Pseudo-boehmite | 70/30 | Butyl levulinate | 84 | 88 |
| C17 | MCM-41 | 20 | Pseudo-boehmite | 50/50 | Butyl levulinate | 81 | 82 |
| C18 | MCM-22 | 50 | Pseudo-boehmite | 50/50 | Butyl levulinate | 83 | 89 |
| C5A | 5A | 2 | Alumina | 50/50 | Levulinic acid | 35 | 17 |

Example VII-1

500 g of bagasse was weighed and placed into a pressured reactor, 5000 g of water was added, and a 5 mol/L of hydrochloric acid solution having 5 wt % of water was further added. The temperature was increased to 180 degree Celsius for reaction for 1 h, cooled, and the cooled reaction liquor was filtrated to provide a filter cake and a filtrate, which filtrate was a hydrolysate of cellulose. After reaction, the reaction resultant was analyzed using a mass spectra, which showed that the main product was levulinic acid at an output of 160 g.

5 g of $SO_4^{2-}/ZrO_2$ catalyst which had been dried at a temperature of 120 degree Celsius for 12 h to remove water was weighed and placed into a fixed bed reactor. The reaction substrate was levulinic acid

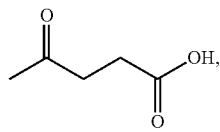

with a WHSV of 0.3 hour$^{-1}$, a hydrogen pressure of 1.0 MPa, a flow rate of 50 ml min$^{-1}$ and a temperature of 400 degree Celsius. After reaction, the reaction result was qualitatively analyzed using mass spectra, and was quantitatively analyzed using chromatogram. The conversion of substrate was 99%, the selectivity to BTX aromatics was 93%, and the yield of carbon as BTX aromatics was 92%.

Example VII-2

5 g of $S_2O_8^{2-}/ZrO_2$ catalyst, which had been dried at a temperature of 120 degree Celsius for 12 h to remove water, was weighed and placed into a fixed bed reactor. The reaction substrate was acetoacetic acid

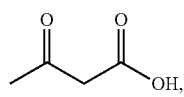

with a WHSV of 1.0 hour$^{-1}$, a hydrogen pressure of 1.0 MPa, a flow rate of 20 ml min$^{-1}$ and a temperature of 450 degree Celsius. After reaction, the reaction result was qualitatively analyzed using mass spectra, and was quantitatively analyzed using chromatogram. The conversion of substrate was 90%, the selectivity to BTX aromatics was 93%, and the yield of carbon as BTX aromatics was 84%.

Example VII-3

5 g of $SO_4^{2-}/TiO_2$ catalyst, which had been dried at a temperature of 120 degree Celsius for 12 h to remove water, was weighed and placed into a fixed bed reactor. The reaction substrate was levulinic acid

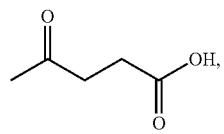

with a WHSV of 3.0 hour$^{-1}$, a hydrogen pressure of 1.0 MPa, a flow rate of 20 ml min$^{-1}$ and a temperature of 400 degree Celsius. After reaction, the reaction result was qualitatively analyzed using mass spectra, and was quantitatively analyzed using chromatogram. The conversion of substrate was 89%, the selectivity to BTX aromatics was 87%, and the yield of carbon as BTX aromatics was 77%.

Example VII-4

5 g of $SO_4^{2-}/ZrO_2$—$Fe_3O_4$ catalyst, which had been dried at a temperature of 120 degree Celsius for 12 h to remove water, was weighed and placed into a fixed bed reactor. The reaction substrate was ethyl acetoacetate

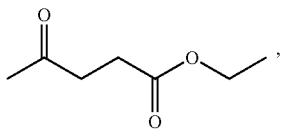

with a WHSV of 5.0 hour$^{-1}$, a hydrogen pressure of 1.0 MPa, a flow rate of 20 ml min$^{-1}$ and a temperature of 500 degree Celsius. After reaction, the reaction result was qualitatively analyzed using mass spectra, and was quantitatively analyzed using chromatogram. The conversion of substrate was 86%, the selectivity to BTX aromatics was 83%, and the yield of carbon as BTX aromatics was 71%.

Example VII-5

5 g of Pt/$SO_4^{2-}/TiO_2$ catalyst, which had been dried at a temperature of 120 degree Celsius for 12 h to remove water, was weighed and placed into a fixed bed reactor. The reaction substrate was methyl levulinate

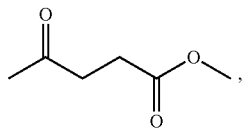

with a WHSV of 2.0 hour$^{-1}$, a hydrogen pressure of 3.0 MPa, a flow rate of 20 ml min$^{-1}$ and a temperature of 450 degree Celsius. After reaction, the reaction result was qualitatively analyzed using mass spectra, and was quantitatively analyzed using chromatogram. The conversion of substrate was 85%, the selectivity to BTX aromatics was 82%, and the yield of carbon as BTX aromatics was 70%.

Example VII-6

5 g of $SO_4^{2-}/TiO_2$—$ZrO_2$ catalyst, which had been dried at a temperature of 120 degree Celsius for 12 h to remove water, was weighed and placed into a fixed bed reactor. The reaction substrate was methyl acetobutyrate

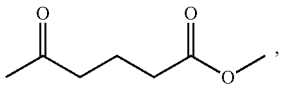

with a WHSV of 0.8 hour$^{-1}$, a hydrogen pressure of 4.0 MPa, a flow rate of 40 ml min$^{-1}$ and a temperature of 400 degree Celsius. After reaction, the reaction result was qualitatively analyzed using mass spectra, and was quantitatively analyzed using chromatogram. The conversion of substrate was 89%, the selectivity to BTX aromatics was 87%, and the yield of carbon as BTX aromatics was 77%.

Example VII-7

5 g of $SO_4^{2-}/TiO_2$—$Al_2O_3$ catalyst, which had been dried at a temperature of 120 degree Celsius for 12 h to remove water, was weighed and placed into a fixed bed reactor. The reaction substrate was octyl levulinate

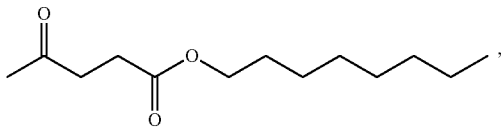 [SMILES: CCCCCCCCOC(=O)CCC(C)=O]

with a WHSV of 3.0 hour$^{-1}$, a hydrogen pressure of 1.0 MPa, a flow rate of 20 ml min$^{-1}$ and a temperature of 400 degree Celsius. After reaction, the reaction result was qualitatively analyzed using mass spectra, and was quantitatively analyzed using chromatogram. The conversion of substrate was 87%, the selectivity to BTX aromatics was 85%, and the yield of carbon as BTX aromatics was 74%.

Example VII-8

5 g of $SO_4^{2-}/ZrO_2$—$Fe_2O_3$—$Cr_2O_3$ catalyst, which had been dried at a temperature of 120 degree Celsius for 12 h to remove water, was weighed and placed into a fixed bed reactor. The reaction substrate was ethyl levulinate

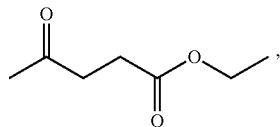

with a WHSV of 2.0 hour$^{-1}$, a hydrogen pressure of 1.0 MPa, a flow rate of 50 ml min$^{-1}$ and a temperature of 450 degree Celsius. After reaction, the reaction result was qualitatively analyzed using mass spectra, and was quantitatively analyzed using chromatogram. The conversion of substrate was 91%, the selectivity to BTX aromatics was 85%, and the yield of carbon as BTX aromatics was 77%.

Example VII-9

5 g of $SbF_5/SiO_2$—$Al_2O_3$ catalyst, which had been dried at a temperature of 120 degree Celsius for 12 h to remove water, was weighed and placed into a fixed bed reactor. The reaction substrate was butyl levulinate

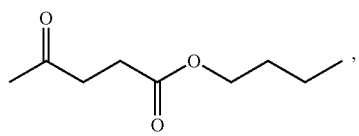

with a WHSV of 3.0 hour$^{-1}$, a hydrogen pressure of 1.0 MPa, a flow rate of 20 ml min$^{-1}$ and a temperature of 470 degree Celsius. After reaction, the reaction result was qualitatively analyzed using mass spectra, and was quantitatively analyzed using chromatogram. The conversion of substrate was 98%, the selectivity to BTX aromatics was 89%, and the yield of carbon as BTX aromatics was 87%.

Example VII-10

600 g of corn stover was weighed and placed into a pressured reactor, 3400 g of ethanol was added, and a 5 mol/L of sulphuric acid solution having 7 wt % of water was further added. The temperature was increased to 180 degree Celsius for reaction for 45 minutes, cooled, and the cooled reaction liquor was filtrated to provide a filter cake and a filtrate, which filtrate was a hydrolysate of cellulose. After reaction, the reaction resultant was analyzed using a mass spectra, which showed that the main product was ethyl levulinate wherein the amount of the levulinate group generated in the product was 180 g.

5 g of $SO_4^{2-}/TiO_2$—$WO_3$ catalyst, which had been dried at a temperature of 120 degree Celsius for 12 h to remove water, was weighed and placed into a fixed bed reactor. The reaction substrate was ethyl levulinate

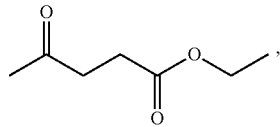

with a WHSV of 1.0 hour$^{-1}$, a hydrogen pressure of 1.0 MPa, a flow rate of 20 ml min$^{-1}$ and a temperature of 500 degree Celsius. After reaction, the reaction result was qualitatively analyzed using mass spectra, and was quantitatively

Example VII-11

5 g of $SO_4^{2-}/TiO_2$—$WO_3$ catalyst, which had been dried at a temperature of 120 degree Celsius for 12 h to remove water, was weighed and placed into a fixed bed reactor. The reaction substrate was decyl levulinate

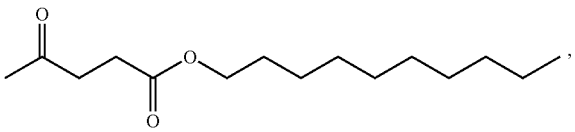 [SMILES: CCCCCCCCCCOC(=O)CCC(C)=O]

with a WHSV of 1.0 hour$^{-1}$, a hydrogen pressure of 1.0 MPa, a flow rate of 20 ml min$^{-1}$ and a temperature of 380 degree Celsius. After reaction, the reaction result was qualitatively analyzed using mass spectra, and was quantitatively analyzed using chromatogram. The conversion of substrate was 91%, the selectivity to BTX aromatics was 84%, and the yield of carbon as BTX aromatics was 76%.

Example VII-12

5 g of $SO_4^{2-}/TiO_2$—$MoO_3$ catalyst, which had been dried at a temperature of 120 degree Celsius for 12 h to remove water, was weighed and placed into a fixed bed reactor. The reaction substrate was methyl levulinate

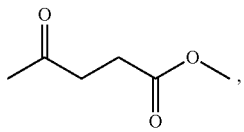

with a WHSV of 2.0 hour$^{-1}$, a hydrogen pressure of 1.0 MPa, a flow rate of 20 ml min$^{-1}$ and a temperature of 380 degree Celsius. After reaction, the reaction result was qualitatively analyzed using mass spectra, and was quantitatively analyzed using chromatogram. The conversion of substrate was 86%, the selectivity to BTX aromatics was 83%, and the yield of carbon as BTX aromatics was 71%.

Example VII-13

5 g of $BiF_3/Al_2O_3$—$B_2O_3$ catalyst, which had been dried at a temperature of 120 degree Celsius for 12 h to remove water, was weighed and placed into a fixed bed reactor. The reaction substrate was methyl levulinate, with a WHSV of 1.0 hour$^{-1}$, a hydrogen pressure of 1.0 MPa, a flow rate of 20 ml min$^{-1}$ and a temperature of 420 degree Celsius. After reaction, the reaction result was qualitatively analyzed using mass spectra, and was quantitatively analyzed using chromatogram. The conversion of substrate was 96%, the selectivity to BTX aromatics was 86%, and the yield of carbon as BTX aromatics was 83%.

Example VII-14

5 g of $NbF_3/Al_2O_3$—$B_2O_3$ catalyst, which had been dried at a temperature of 120 degree Celsius for 12 h to remove water, was weighed and placed into a fixed bed reactor. The reaction substrate was methyl acetohexanoate

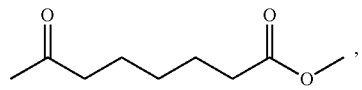

with a WHSV of 2.0 hour$^{-1}$, a hydrogen pressure of 1.0 MPa, a flow rate of 20 ml min$^{-1}$ and a temperature of 360 degree Celsius. After reaction, the reaction result was qualitatively analyzed using mass spectra, and was quantitatively analyzed using chromatogram. The conversion of substrate was 88%, the selectivity to BTX aromatics was 94%, and the yield of carbon as BTX aromatics was 83%.

Example VII-15

5 g of $SO_4^{2-}/ZrO_2$—$Fe_2O_3$—$MnO_2$ catalyst, which had been dried at a temperature of 120 degree Celsius for 12 h to remove water, was weighed and placed into a fixed bed reactor. The reaction substrate was butyl levulinate

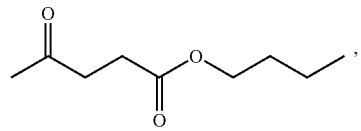

with a WHSV of 2.0 hour$^{-1}$, a hydrogen pressure of 1.0 MPa, a flow rate of 20 ml min$^{-1}$ and a temperature of 400 degree Celsius. After reaction, the reaction result was qualitatively analyzed using mass spectra, and was quantitatively analyzed using chromatogram. The conversion of substrate was 89%, the selectivity to BTX aromatics was 87%, and the yield of carbon as BTX aromatics was 77%.

Example VII-16

5 g of $SO_4^{2-}/ZrO_2$—$Fe_2O_3$—$Cr_2O_3$ catalyst, which had been dried at a temperature of 120 degree Celsius for 12 h to remove water, was weighed and placed into a fixed bed reactor. The reaction substrate was butyl levulinate, with a WHSV of 1.0 hour$^{-1}$, a hydrogen pressure of 1.0 MPa, a flow rate of 20 ml min$^{-1}$ and a temperature of 380 degree Celsius. After reaction, the reaction result was qualitatively analyzed using mass spectra, and was quantitatively analyzed using chromatogram. The conversion of substrate was 92%, the selectivity to BTX aromatics was 86%, and the yield of carbon as BTX aromatics was 79%.

Example VII-17

5 g of $AlCl_3$—$CuCl_2$ catalyst, which had been dried at a temperature of 120 degree Celsius for 12 h to remove water, was weighed and placed into a fixed bed reactor. The reaction substrate was butyl levulinate, with a WHSV of 3.5 hour$^{-1}$, a hydrogen pressure of 1.0 MPa, a flow rate of 20 ml min$^{-1}$ and a temperature of 400 degree Celsius. After reaction, the reaction result was qualitatively analyzed using mass spectra, and was quantitatively analyzed using chromatogram. The conversion of substrate was 87%, the selectivity to BTX aromatics was 82%, and the yield of carbon as BTX aromatics was 71%.

TABLE VII-1

| Examples | Substrate | Catalyst | Conversion/% | Selectivity to BTX/% |
|---|---|---|---|---|
| 1 | Levulinic acid | $SO_4^{2-}/ZrO_2$ | 99 | 93 |
| 2 | Acetoacetic acid | $S_2O_8^{2-}/ZrO_2$ | 90 | 93 |
| 3 | Levulinic acid | $SO_4^{2-}/TiO_2$ | 89 | 87 |
| 4 | Ethyl acetoacetate | $SO_4^{2-}/ZrO_2$—$Fe_3O_4$ | 86 | 83 |
| 5 | Methyl levulinate | $Pt/SO_4^{2-}/TiO_2$ | 85 | 82 |
| 6 | Methyl acetobutyrate | $SO_4^{2-}/TiO_2$—$ZrO_2$ | 89 | 87 |
| 7 | Octyl levulinate | $SO_4^{2-}/TiO_2$—$Al_2O_3$ | 87 | 85 |
| 8 | Ethyl levulinate | $SO_4^{2-}/ZrO_2$—$Fe_2O_3$—$Cr_2O_3$ | 91 | 85 |
| 9 | Butyl levulinate | $SbF_5/SiO_2$—$Al_2O_3$ | 98 | 89 |
| 10 | Ethyl levulinate | $SO_4^{2-}/TiO_2$—$WO_3$ | 89 | 86 |
| 11 | Decyl levulinate | $SO_4^{2-}/ZrO_2$—$WO_3$ | 91 | 84 |
| 12 | Methyl levulinate | $SO_4^{2-}/TiO_2$—$MoO_3$ | 86 | 83 |
| 13 | Methyl levulinate | $BiF_3/Al_2O_3$—$B_2O_3$ | 96 | 86 |
| 14 | Methyl acetohexanoate | $NbF_3/Al_2O_3$—$B_2O_3$ | 88 | 94 |
| 15 | Butyl levulinate | $SO_4^{2-}/ZrO_2$—$Fe_2O_3$—$MnO_2$ | 89 | 87 |
| 16 | Butyl levulinate | $SO_4^{2-}/ZrO_2$—$Fe_2O_3$—$Cr_2O_3$ | 92 | 86 |
| 17 | Butyl levulinate | $AlCl_3$—$CuCl_2$ | 87 | 82 |

Example VIII-1

35 g of ZSM-5 having a ratio of Si:Al of 25 was mixed with 35 g of an auxiliary of γ-alumina, 2.7 g of sesbania powder was added, and mixed homogeneously. Then, 48 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, calcined at a temperature of 500 degree Celsius for 2 h, then was immersed with equal-volume of $Zn(NO_3)_2$ in an addition amount of Zn of 1%, and was dried and calcined to provide a molecular sieve catalyst.

600 g of corn stover was weighed and placed into a pressured reactor, 7000 g of water was added, and a 5 mol/L of sulphuric acid solution having 7 wt % of water was further added. The temperature was increased to 200 degree Celsius for reaction for 45 minutes, cooled, and the cooled reaction liquor was filtrated to provide a filter cake and a filtrate, which filtrate was a hydrolysate of cellulose. After reaction, the reaction resultant was analyzed using a mass spectra, which showed that the main product was levulinic acid at an output of 240 g.

The catalyst was evaluated for activity on a fixed bed, under reaction conditions of: 3 g of catalyst, the reaction substrate being levulinic acid, a WHSV of 1.0 hour$^{-1}$, a hydrogen pressure of 1.0 MPa, a flow rate of 50 ml min$^{-1}$, and a temperature of 450 degree Celsius. After reaction, the conversion of the reaction substrate was 99%, the selectivity to BTX aromatics was 93%, and the yield of carbon as BTX aromatics was 92%.

Example VIII-2

35 g of ZSM-5 having a ratio of Si:Al of 50 was mixed with 35 g of pseudo-boehmite, 2.7 g of sesbania powder was added, and mixed homogeneously. Then, 48 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, calcined at a temperature of 500 degree Celsius for 2 h, then was immersed with equal-volume of $Cu(NO_3)_2$ in an addition amount of Cu of 2%, and was dried and calcined to provide a molecular sieve catalyst C2.

The catalyst was evaluated for activity on a fixed bed, under reaction conditions of: 3 g of catalyst, the reaction substrate being levulinic acid, a WHSV of 1.0 hour$^{-1}$, a hydrogen pressure of 1.0 MPa, a flow rate of 50 ml min$^{-1}$, and a temperature of 420 degree Celsius. After reaction, the conversion of the reaction substrate was 92%, the selectivity to BTX aromatics was 95%, and the yield of carbon as BTX aromatics was 87%.

Example VIII-3

300 g of wood was weighed and placed into a pressured reactor, 3000 g of ethanol was added, and a 5 mol/L of sulphuric acid solution having 7 wt % of ethanol was further added. The temperature was increased to 200 degree Celsius for reaction for 30 minutes, cooled, and the cooled reaction liquor was filtrated to provide a filter cake and a filtrate, which filtrate was a hydrolysate of cellulose. After reaction, the reaction resultant was analyzed using a mass spectra, which showed that the main product was levulinic acid at an output of 105 g.

35 g of ZSM-5 having a ratio of Si:Al of 150 was mixed with 35 g of pseudo-boehmite, 2.7 g of sesbania powder was added, and mixed homogeneously. Then, 48 g of an aqueous solution of nitric acid comprising 5.5 wt % of nitric acid was added, mixed and kneaded for shaping, during which kneading $Ga(NO_3)_2$ was added in an addition amount of Ga of 1% based on the weight of the molecular sieve, and extruded as a strip. The catalyst precursor obtained was dried at a temperature of 120 degree Celsius for 8 h, and calcined at a temperature of 500 degree Celsius for 2 h, to provide a molecular sieve catalyst C3.

The catalyst was evaluated for activity on a fixed bed, under reaction conditions of: 3 g of catalyst, the reaction substrate being levulinic acid, a WHSV of 1.5 hour$^{-1}$, a hydrogen pressure of 1.0 MPa, a flow rate of 50 ml min$^{-1}$, and a temperature of 420 degree Celsius.

After reaction, the conversion of the reaction substrate was 96%, the selectivity to BTX aromatics was 91%, and the yield of carbon as BTX aromatics was 87%.

Example VIII-4

80 g of ZSM-5 having a ratio of Si:Al of 500 was mixed with 20 g of pseudo-boehmite, 3.9 g of sesbania powder was added, and mixed homogeneously. Then, 68.6 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, calcined at a temperature of 500 degree Celsius for 2 h, then was immersed with equal-volume of boric acid in an addition amount of B of 1%, and was dried and calcined to provide a molecular sieve catalyst C4.

The catalyst was evaluated for activity on a fixed bed, under reaction conditions of: 3 g of catalyst, the reaction substrate being levulinic acid, a WHSV of 1.0 hour$^{-1}$, a hydrogen pressure of 4.0 MPa, a flow rate of 50 ml min$^{-1}$, and a temperature of 470 degree Celsius. After reaction, the conversion of the reaction substrate was 98%, the selectivity to BTX aromatics was 87%, and the yield of carbon as BTX aromatics was 85%.

Example VIII-5

80 g of ZSM-38 having a ratio of Si:Al of 150 was mixed with 20 g of silica sol, 3.9 g of sesbania powder was added, and mixed homogeneously. Then, 68.6 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, calcined at a temperature of 500 degree Celsius for 2 h, then was immersed with equal-volume of ammonium molybdate in an addition amount of Mo of 4%, and was dried and calcined to provide a molecular sieve catalyst C5.

The catalyst was evaluated for activity on a fixed bed, under reaction conditions of: 3 g of catalyst, the reaction substrate being methyl levulinate, a WHSV of 1.0 hour$^{-1}$, a hydrogen pressure of 3.0 MPa, a flow rate of 50 ml min$^{-1}$, and a temperature of 380 degree Celsius. After reaction, the conversion of the reaction substrate was 91%, the selectivity to BTX aromatics was 74%, and the yield of carbon as BTX aromatics was 90%.

Example VIII-6

80 g of ZSM-11 having a ratio of Si:Al of 150 was mixed with 20 g of silica sol, 3.9 g of sodium carboxymethylcellulose was added, and mixed homogeneously. Then, 68.6 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, calcined at a temperature of 500 degree Celsius for 2 h, then was immersed with equal-volume of lanthanum nitrate in an addition amount of La of 1%, and was dried and calcined to provide a molecular sieve catalyst C6.

The catalyst was evaluated for activity on a fixed bed, under reaction conditions of: 3 g of catalyst, the reaction substrate being methyl levulinate, a WHSV of 5.0 hour$^{-1}$, a hydrogen pressure of 1.0 MPa, a flow rate of 50 ml min$^{-1}$, and a temperature of 480 degree Celsius. After reaction, the conversion of the reaction substrate was 96%, the selectivity to BTX aromatics was 89%, and the yield of carbon as BTX aromatics was 85%.

Example VIII-7

70 g of ZSM-11 having a ratio of Si:Al of 100 was mixed with 30 g of kaolin, 3.9 g of sesbania powder was added, and mixed homogeneously. Then, 68.6 g of an aqueous solution of phosphoric acid comprising 5.5 wt % of phosphoric acid was added, mixed and kneaded for shaping, and extruded as a strip. The catalyst precursor obtained was dried at a temperature of 120 degree Celsius for 8 h, calcined at a temperature of 500 degree Celsius for 2 h, then was immersed with equal-volume of cerous nitrate in an addition amount of Ce of 1%, and was dried and calcined to provide a molecular sieve catalyst C6.

The catalyst was evaluated for activity on a fixed bed, under reaction conditions of: 3 g of catalyst, the reaction substrate being ethyl levulinate, a WHSV of 3.0 hour$^{-1}$, a hydrogen pressure of 1.0 MPa, a flow rate of 50 ml min$^{-1}$, and a temperature of 550 degree Celsius. After reaction, the conversion of the reaction substrate was 99%, the selectivity to BTX aromatics was 83%, and the yield of carbon as BTX aromatics was 82%.

Example VIII-8

50 g of ZSM-23 having a ratio of Si:Al of 100 was mixed with 50 g of alumina, 3.9 g of sesbania powder was added, and mixed homogeneously. Then, 68.6 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, calcined at a temperature of 500 degree Celsius for 2 h, then was immersed with equal-volume of tin chloride in an addition amount of Sn of 1%, and was dried and calcined to provide a molecular sieve catalyst C6.

The catalyst was evaluated for activity on a fixed bed, under reaction conditions of: 3 g of catalyst, the reaction substrate being ethyl levulinate, a WHSV of 1.0 hour$^{-1}$, a hydrogen pressure of 5.0 MPa, a flow rate of 20 ml min$^{-1}$, and a temperature of 400 degree Celsius. After reaction, the conversion of the reaction substrate was 99%, the selectivity to BTX aromatics was 91%, and the yield of carbon as BTX aromatics was 90%.

Example VIII-9

60 g ZSM-5 powder having a ratio of Si:Al of 50 was weighed and ion exchanged in a 180 ml of aqueous solution comprising lanthanum nitrate and cerous nitrate at a temperature of 90 degree Celsius for 2 h. The metal contents of La and Ce in the solution are respectively 1 wt % of the solid molecular sieve powder. Drying was conducted after exchange, and 35 g of ZSM-5 having a ratio of Si:Al of 50 was mixed with 35 g of an auxiliary of γ-alumina, 2.7 g of sesbania powder was added, and mixed homogeneously. Then, 48 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide a molecular sieve catalyst C9.

The catalyst was evaluated for activity on a fixed bed, under reaction conditions of: 3 g of catalyst, the reaction substrate being butyl levulinate, a WHSV of 2.0 hour$^{-1}$, a hydrogen pressure of 1.0 MPa, a flow rate of 50 ml min$^{-1}$, and a temperature of 450 degree Celsius. After reaction, the conversion of the reaction substrate was 96%, the selectivity to BTX aromatics was 89%, and the yield of carbon as BTX aromatics was 85%.

Example VIII-10

35 g of Y molecular sieve having a ratio of Si:Al of 6 was mixed with 35 g of an auxiliary of γ-alumina, 2.7 g of sodium carboxymethylcellulose was added, and mixed homogeneously. Then, 48 g of an aqueous solution of nitric acid comprising 5.5 wt % of nitric acid was added, mixed and kneaded for shaping, during which kneading copper nitrate and zinc nitrate were added in an addition amount of copper and zinc of respectively 1% and 1% by weight based on the weight of the molecular sieve solid, and extruded as a strip. The catalyst precursor obtained was dried at a temperature of 120 degree Celsius for 8 h, and calcined at a temperature of 500 degree Celsius for 2 h, to provide a molecular sieve catalyst C10.

The catalyst was evaluated for activity on a fixed bed, under reaction conditions of: 3 g of catalyst, the reaction substrate being butyl levulinate, a WHSV of 1.0 hour$^{-1}$, a hydrogen pressure of 1.0 MPa, a flow rate of 50 ml min$^{-1}$, and a temperature of 450 degree Celsius. After reaction, the conversion of the reaction substrate was 91%, the selectivity to BTX aromatics was 81%, and the yield of carbon as BTX aromatics was 74%.

Example VIII-11

60 g of Y molecular sieve having a ratio of Si:Al of 8 was mixed with 40 g of an auxiliary of γ-alumina, 3.9 g of sesbania powder was added, and mixed homogeneously. Then, 68.6 g of an aqueous solution of phosphoric acid comprising 5.5 wt % of phosphoric acid was added, mixed and kneaded for shaping, during which kneading silver nitrate was added in an addition amount of Ag of 1% based on the weight of the molecular sieve solid, and extruded as a strip. The catalyst precursor obtained was dried at a temperature of 120 degree Celsius for 8 h, and calcined at a temperature of 500 degree Celsius for 2 h, to provide a molecular sieve catalyst C11.

The catalyst was evaluated for activity on a fixed bed, under reaction conditions of: 3 g of catalyst, the reaction substrate being methyl levulinate, a WHSV of 3.0 hour$^{-1}$, a hydrogen pressure of 1.0 MPa, a flow rate of 50 ml min$^{-1}$, and a temperature of 450 degree Celsius. After reaction, the conversion of the reaction substrate was 93%, the selectivity to BTX aromatics was 88%, and the yield of carbon as BTX aromatics was 82%.

Example VIII-12

60 g Y molecular sieve having a ratio of Si:Al of 8 was weighed and ion exchanged in a 180 ml of aqueous solution comprising nickel nitrate at a temperature of 90 degree Celsius for 2 h. The metal content of Ni in the solution is 5 wt % of the solid molecular sieve. Drying was made after exchange, 70 g of Y molecular sieve having a ratio of Si:Al of 8 was mixed with 30 g of pseudo-boehmite, 3.9 g of sesbania powder was added, and mixed homogeneously. Then, 68.6 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide a molecular sieve catalyst C12.

The catalyst was evaluated for activity on a fixed bed, under reaction conditions of: 3 g of catalyst, the reaction substrate being methyl levulinate, a WHSV of 1.0 hour$^{-1}$, a hydrogen pressure of 1.0 MPa, a flow rate of 50 ml min$^{-1}$, and a temperature of 400 degree Celsius. After reaction, the conversion of the reaction substrate was 94%, the selectivity to BTX aromatics was 89%, and the yield of carbon as BTX aromatics was 84%.

Example VIII-13

180 g Y molecular sieve having a ratio of Si:Al of 8 was weighed and ion exchanged in a 180 ml of aqueous solution comprising gallium nitrate at a temperature of 90 degree Celsius for 2 h. The metal content of Ga in the solution is 2 wt % of the solid molecular sieve. Drying was made after exchange, 80 g of Y molecular sieve having a ratio of Si:Al of 8 was mixed with 20 g of pseudo-boehmite, 3.9 g of sesbania powder was added, and mixed homogeneously. Then, 68.6 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide a molecular sieve catalyst C13.

The catalyst was evaluated for activity on a fixed bed, under reaction conditions of: 3 g of catalyst, the reaction substrate being methyl levulinate, a WHSV of 1.0 hour$^{-1}$, a hydrogen pressure of 4.0 MPa, a flow rate of 50 ml min$^{-1}$, and a temperature of 400 degree Celsius. After reaction, the conversion of the reaction substrate was 86%, the selectivity to BTX aromatics was 87%, and the yield of carbon as BTX aromatics was 75%.

Example VIII-14

50 g of beta having a ratio of Si:Al of 30 was mixed with 50 g of pseudo-boehmite, 3.9 g of sesbania powder was added, and mixed homogeneously. Then, 68.6 g of an aqueous solution of nitric acid comprising 5.5 wt % of nitric acid was added, mixed and kneaded for shaping, during which kneading magnesium chloride was added, and extruded as a strip. The catalyst precursor obtained was dried at a temperature of 120 degree Celsius for 8 h, and calcined at a temperature of 500 degree Celsius for 2 h, to provide a molecular sieve catalyst C15.

The catalyst was evaluated for activity on a fixed bed, under reaction conditions of: 3 g of catalyst, the reaction substrate being methyl levulinate, a WHSV of 1.0 hour$^{-1}$, a hydrogen pressure of 1.0 MPa, a flow rate of 50 ml min$^{-1}$, and a temperature of 400 degree Celsius. After reaction, the conversion of the reaction substrate was 91%, the selectivity to BTX aromatics was 82%, and the yield of carbon as BTX aromatics was 75%.

Example VIII-15

60 g of beta having a ratio of Si:Al of 50 was mixed with 40 g of pseudo-boehmite, 3.9 g of sesbania powder was added, and mixed homogeneously. Then, 68.6 g of an aqueous solution of acetic acid comprising 5.5 wt % of acetic acid was added, mixed and kneaded for shaping, and extruded as a strip. The catalyst precursor obtained was dried at a temperature of 120 degree Celsius for 8 h, calcined at a temperature of 500 degree Celsius for 2 h, then was immersed with equal-volume of ammonium molybdate in an addition amount of Mo of 6%, and was dried and calcined to provide a molecular sieve catalyst C15.

The catalyst was evaluated for activity on a fixed bed, under reaction conditions of: 3 g of catalyst, the reaction substrate being butyl levulinate, a WHSV of 1.0 hour$^{-1}$, a hydrogen pressure of 1.0 MPa, a flow rate of 50 ml min$^{-1}$, and a temperature of 460 degree Celsius. After reaction, the conversion of the reaction substrate was 98%, the selectivity to BTX aromatics was 87%, and the yield of carbon as BTX aromatics was 85%.

Example VIII-16

70 g of beta having a ratio of Si:Al of 100 was mixed with 30 g of pseudo-boehmite, 3.9 g of sesbania powder was added, and mixed homogeneously. Then, 68.6 g of an aqueous solution of acetic acid comprising 5.5 wt % of acetic acid was added, mixed and kneaded for shaping, and extruded as a strip. The catalyst precursor obtained was dried at a temperature of 120 degree Celsius for 8 h, calcined at a temperature of 500 degree Celsius for 2 h, then was immersed with equal-volume of niobium nitrate in an addition amount of Nb of 1%, and was dried and calcined to provide a molecular sieve catalyst C16.

The catalyst was evaluated for activity on a fixed bed, under reaction conditions of: 3 g of catalyst, the reaction substrate being butyl levulinate, a WHSV of 1.0 hour$^{-1}$, a hydrogen pressure of 1.0 MPa, a flow rate of 50 ml min$^{-1}$, and a temperature of 400 degree Celsius. After reaction, the conversion of the reaction substrate was 94%, the selectivity to BTX aromatics was 88%, and the yield of carbon as BTX aromatics was 83%.

Example VIII-17

50 g of MCM-41 having a ratio of Si:Al of 20 was mixed with 50 g of pseudo-boehmite, 3.9 g of sesbania powder was added, and mixed homogeneously. Then, 68.6 g of an aqueous solution of acetic acid comprising 5.5 wt % of acetic acid was added, mixed and kneaded for shaping, and extruded as a strip. The catalyst precursor obtained was dried at a temperature of 120 degree Celsius for 8 h, calcined at a temperature of 500 degree Celsius for 2 h, then was immersed with equal-volume of ammonium tungstate in an addition amount of W of 1%, and was dried and calcined to provide a molecular sieve catalyst C17.

The catalyst was evaluated for activity on a fixed bed, under reaction conditions of: 3 g of catalyst, the reaction substrate being butyl levulinate, a WHSV of 1.0 hour$^{-1}$, a hydrogen pressure of 1.0 MPa, a flow rate of 50 ml min$^{-1}$, and a temperature of 400 degree Celsius. After reaction, the conversion of the reaction substrate was 91%, the selectivity to BTX aromatics was 82%, and the yield of carbon as BTX aromatics was 75%.

Example VIII-18

50 g of MCM-22 having a ratio of Si:Al of 50 was mixed with 50 g of pseudo-boehmite, 3.9 g of sesbania powder was added, and mixed homogeneously. Then, 68.6 g of an aqueous solution of acetic acid comprising 5.5 wt % of acetic acid was added, mixed and kneaded for shaping, and extruded as a strip. The catalyst precursor obtained was dried at a temperature of 120 degree Celsius for 8 h, calcined at a temperature of 500 degree Celsius for 2 h, then was immersed with equal-volume of manganous nitrate in an addition amount of Mn of 3%, and was dried and calcined to provide a molecular sieve catalyst C18.

The catalyst was evaluated for activity on a fixed bed, under reaction conditions of: 3 g of catalyst, the reaction substrate being butyl levulinate, a WHSV of 1.0 hour$^{-1}$, a hydrogen pressure of 1.0 MPa, a flow rate of 50 ml min$^{-1}$, and a temperature of 400 degree Celsius. After reaction, the conversion of the reaction substrate was 93%, the selectivity to BTX aromatics was 89%, and the yield of carbon as BTX aromatics was 83%.

Comparative Example VIII-1

Comparative example VIII-1 was practiced to illustrate the synthesis of a catalyst comprising 5A type as the main active component, the preparation of catalyst and the properties thereof for aromatization of levulinic acid. The specific reactants formulation and the experimental method were provided as follows:

35 g of 5A molecular sieve having a ratio of Si:Al of 2 was mixed with 35 g of an auxiliary of γ-alumina, 2.7 g of sesbania powder was added, and mixed homogeneously. Then, 48 g of an aqueous solution of nitric acid comprising 5.5 wt % of nitric acid was added, mixed and kneaded for shaping, and extruded as a strip. The catalyst precursor obtained was dried at a temperature of 120 degree Celsius for 8 h, and calcined at a temperature of 500 degree Celsius for 2 h, to provide a molecular sieve catalyst C5A.

The catalyst was evaluated for activity on a fixed bed, under reaction conditions of: 3 g of catalyst, the reaction substrate being levulinic acid, a WHSV of 1.0 hour$^{-1}$, a hydrogen pressure of 1.0 MPa, a flow rate of 50 ml min$^{-1}$, a temperature of 400 degree Celsius. After reaction, calculation of the reaction result showed that the conversion of the reaction substrate was 35%, the selectivity to BTX aromatics was 17%, and the yield of carbon as BTX aromatics was 6%.

TABLE VIII-1

| Catalyst | Molecular sieve | Ratio of Si:Al | Auxiliary | Substrate | Conversion/% | Selectivity to BTX/% |
|---|---|---|---|---|---|---|
| Comparative example | 5A | 2 | — | Levulinic acid | 35 | 17 |
| C1 | ZSM-5 | 25 | Zn | Levulinic acid | 99 | 93 |
| C2 | ZSM-5 | 50 | Cu | Levulinic acid | 92 | 95 |
| C3 | ZSM-5 | 150 | Ga | Levulinic acid | 96 | 91 |
| C4 | ZSM-5 | 500 | B | Levulinic acid | 98 | 87 |
| C5 | ZSM-38 | 150 | Mo | Methyl levulinate | 91 | 74 |
| C6 | ZSM-11 | 150 | La | Methyl levulinate | 96 | 89 |
| C7 | ZSM-11 | 100 | Ce | Ethyl levulinate | 99 | 83 |
| C8 | ZSM-23 | 100 | Sn | Ethyl levulinate | 99 | 91 |
| C9 | ZSM-5 | 100 | La—Ce | Butyl levulinate | 96 | 89 |

TABLE VIII-1-continued

| Catalyst | Molecular sieve | Ratio of Si:Al | Auxiliary | Substrate | Conversion/% | Selectivity to BTX/% |
|---|---|---|---|---|---|---|
| C10 | Y | 6 | Cu—Zn | Butyl levulinate | 91 | 81 |
| C11 | Y | 8 | Ag | Methyl levulinate | 93 | 88 |
| C12 | Y | 8 | Ni | Methyl levulinate | 94 | 89 |
| C13 | Y | 8 | Ga | Methyl levulinate | 86 | 87 |
| C14 | beta | 30 | Mg | Methyl levulinate | 91 | 82 |
| C15 | beta | 50 | Mo | Butyl levulinate | 98 | 87 |
| C16 | beta | 100 | Nb | Butyl levulinate | 94 | 88 |
| C17 | MCM-41 | 20 | W | Butyl levulinate | 91 | 82 |
| C18 | MCM-22 | 50 | Mn | Butyl levulinate | 93 | 89 |

Example IX-1

50 g of bagasse was weighed and placed into a pressured reactor, 500 g of water was added, and a 5 mol/L of hydrochloric acid solution having 5 wt % of water was further added. The temperature was increased to 180 degree Celsius for reaction for 1 h, cooled, and the cooled reaction liquor was filtrated to provide a filter cake and a filtrate, which filtrate was a hydrolysate of cellulose. After reaction, the reaction resultant was analyzed using a mass spectra, which showed that the main product was levulinic acid at an output of 16 g.

5 g of WO$_3$/ZrO$_2$ catalyst which had been dried at a temperature of 120 degree Celsius for 12 h to remove water was weighed and placed into a fixed bed reactor. The reaction substrate was levulinic acid

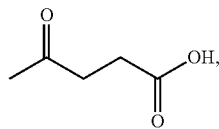

with a WHSV of 0.3 hour$^{-1}$, a hydrogen pressure of 1.0 MPa, a flow rate of 50 ml min$^{-1}$ and a temperature of 450 degree Celsius. After reaction, the reaction result was qualitatively analyzed using mass spectra, and was quantitatively analyzed using chromatogram. The conversion of substrate was 97%, the selectivity to BTX aromatics was 93%, and the yield of carbon as BTX aromatics was 90%.

Example IX-2

5 g of WO$_3$/ZrO$_2$ catalyst which had been dried at a temperature of 120 degree Celsius for 12 h to remove water was weighed and placed into a fixed bed reactor. The reaction substrate was acetoacetic acid

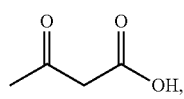

with a WHSV of 1.0 hour$^{-1}$, a hydrogen pressure of 2.0 MPa, a flow rate of 20 ml min$^{-1}$ and a temperature of 420 degree Celsius. After reaction, the reaction result was qualitatively analyzed using mass spectra, and was quantitatively analyzed using chromatogram. The conversion of substrate was 91%, the selectivity to BTX aromatics was 92%, and the yield of carbon as BTX aromatics was 84%.

Example IX-3

5 g of WO$_3$/ZrO$_2$ catalyst which had been dried at a temperature of 120 degree Celsius for 12 h to remove water was weighed and placed into a fixed bed reactor. The reaction substrate was levulinic acid

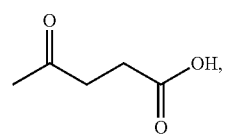

with a WHSV of 3.0 hour$^{-1}$, a hydrogen pressure of 1.0 MPa, a flow rate of 20 ml min$^{-1}$ and a temperature of 400 degree Celsius. After reaction, the reaction result was qualitatively analyzed using mass spectra, and was quantitatively analyzed using chromatogram. The conversion of substrate was 86%, the selectivity to BTX aromatics was 86%, and the yield of carbon as BTX aromatics was 74%.

Example IX-4

5 g of MoO$_3$/ZrO$_2$ catalyst which had been dried at a temperature of 120 degree Celsius for 12 h to remove water was weighed and placed into a fixed bed reactor. The reaction substrate was ethyl acetoacetate

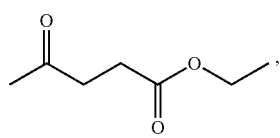

with a WHSV of 5.0 hour$^{-1}$, a hydrogen pressure of 1.0 MPa, a flow rate of 20 ml min$^{-1}$ and a temperature of 500 degree Celsius. After reaction, the reaction result was qualitatively analyzed using mass spectra, and was quantitatively analyzed using chromatogram. The conversion of substrate was 99%, the selectivity to BTX aromatics was 89%, and the yield of carbon as BTX aromatics was 88%.

Example IX-5

5 g of CeO$_2$/ZrO$_2$ catalyst which had been dried at a temperature of 120 degree Celsius for 12 h to remove water was weighed and placed into a fixed bed reactor. The reaction substrate was methyl levulinate

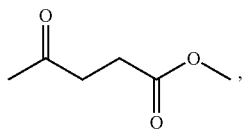

with a WHSV of 2.0 hour$^{-1}$, a hydrogen pressure of 3.0 MPa, a flow rate of 20 ml min$^{-1}$ and a temperature of 450 degree Celsius. After reaction, the reaction result was qualitatively analyzed using mass spectra, and was quantitatively analyzed using chromatogram. The conversion of substrate was 82%, the selectivity to BTX aromatics was 94%, and the yield of carbon as BTX aromatics was 77%.

Example IX-6

5 g of WO$_3$/ZrO$_2$ catalyst which had been dried at a temperature of 120 degree Celsius for 12 h to remove water was weighed and placed into a fixed bed reactor. The reaction substrate was methyl acetobutyrate

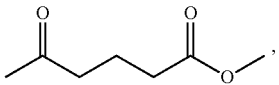

with a WHSV of 0.8 hour$^{-1}$, a hydrogen pressure of 4.0 MPa, a flow rate of 40 ml min$^{-1}$ and a temperature of 400 degree Celsius. After reaction, the reaction result was qualitatively analyzed using mass spectra, and was quantitatively analyzed using chromatogram. The conversion of substrate was 93%, the selectivity to BTX aromatics was 83%, and the yield of carbon as BTX aromatics was 77%.

Example IX-7

5 g of MoO$_3$/ZrO$_2$ catalyst which had been dried at a temperature of 120 degree Celsius for 12 h to remove water was weighed and placed into a fixed bed reactor. The reaction substrate was octyl levulinate

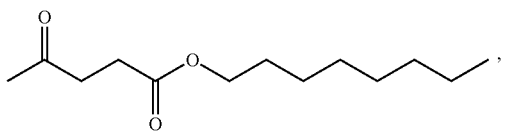 [SMILES: CCCCCCCCOC(=O)CCC(C)=O]

with a WHSV of 3.0 hour$^{-1}$, a hydrogen pressure of 1.0 MPa, a flow rate of 20 ml min$^{-1}$ and a temperature of 400 degree Celsius. After reaction, the reaction result was qualitatively analyzed using mass spectra, and was quantitatively analyzed using chromatogram. The conversion of substrate was 95%, the selectivity to BTX aromatics was 85%, and the yield of carbon as BTX aromatics was 81%.

Example IX-8

5 g of La$_2$O$_3$/ZrO$_2$ catalyst which had been dried at a temperature of 120 degree Celsius for 12 h to remove water was weighed and placed into a fixed bed reactor. The reaction substrate was ethyl levulinate

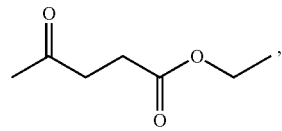

with a WHSV of 2.0 hour$^{-1}$, a hydrogen pressure of 1.0 MPa, a flow rate of 50 ml min$^{-1}$ and a temperature of 450 degree Celsius. After reaction, the reaction result was qualitatively analyzed using mass spectra, and was quantitatively analyzed using chromatogram. The conversion of substrate was 93%, the selectivity to BTX aromatics was 85%, and the yield of carbon as BTX aromatics was 79%.

Example IX-9

5 g of WO$_3$/ZrO$_2$ catalyst which had been dried at a temperature of 120 degree Celsius for 12 h to remove water was weighed and placed into a fixed bed reactor. The reaction substrate was butyl levulinate

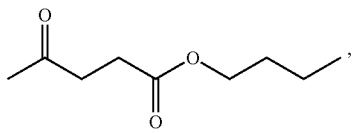

with a WHSV of 3.0 hour$^{-1}$, a hydrogen pressure of 1.0 MPa, a flow rate of 20 ml min$^{-1}$ and a temperature of 470 degree Celsius. After reaction, the reaction result was qualitatively analyzed using mass spectra, and was quantitatively analyzed using chromatogram. The conversion of substrate was 93%, the selectivity to BTX aromatics was 87%, and the yield of carbon as BTX aromatics was 81%.

Example IX-10

60 g of corn stover was weighed and placed into a pressured reactor, 340 g of ethanol was added, and a 5 mol/L of sulphuric acid solution having 7 wt % of water was further added. The temperature was increased to 180 degree Celsius for reaction for 45 minutes, cooled, and the cooled reaction liquor was filtrated to provide a filter cake and a filtrate, which filtrate was a hydrolysate of cellulose. After reaction, the reaction resultant was analyzed using a mass spectra, which showed that the main product was ethyl levulinate wherein the amount of the levulinate group generated in the product was 18 g completely from the stover, comprising 30 wt % of the stover.

5 g of WO$_3$/ZrO$_2$ catalyst which had been dried at a temperature of 120 degree Celsius for 12 h to remove water was weighed and placed into a fixed bed reactor. The reaction substrate was ethyl levulinate

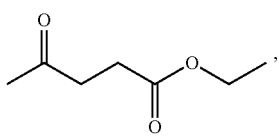

with a WHSV of 1.0 hour$^{-1}$, a hydrogen pressure of 1.0 MPa, a flow rate of 20 ml min$^{-1}$ and a temperature of 500 degree Celsius. After reaction, the reaction result was qualitatively analyzed using mass spectra, and was quantitatively analyzed using chromatogram. The conversion of substrate was 99%, the selectivity to BTX aromatics was 83%, and the yield of carbon as BTX aromatics was 82%.

Example IX-11

5 g of MoO$_3$/ZrO$_2$ catalyst which had been dried at a temperature of 120 degree Celsius for 12 h to remove water was weighed and placed into a fixed bed reactor. The reaction substrate was decyl levulinate

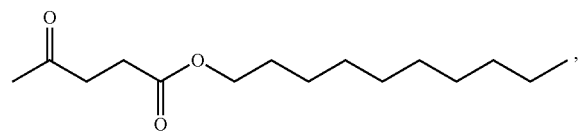 [SMILES: CCCCCCCCCCOC(=O)CCC(C)=O]

with a WHSV of 1.0 hour$^{-1}$, a hydrogen pressure of 1.0 MPa, a flow rate of 20 ml min$^{-1}$ and a temperature of 380 degree Celsius. After reaction, the reaction result was qualitatively analyzed using mass spectra, and was quantitatively analyzed using chromatogram. The conversion of substrate was 96%, the selectivity to BTX aromatics was 84%, and the yield of carbon as BTX aromatics was 81%.

Example IX-12

5 g of MnO$_2$/ZrO$_2$ catalyst which had been dried at a temperature of 120 degree Celsius for 12 h to remove water was weighed and placed into a fixed bed reactor. The reaction substrate was methyl levulinate

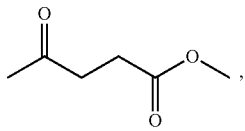

with a WHSV of 2.0 hour$^{-1}$, a hydrogen pressure of 1.0 MPa, a flow rate of 20 ml min$^{-1}$ and a temperature of 380 degree Celsius. After reaction, the reaction result was qualitatively analyzed using mass spectra, and was quantitatively analyzed using chromatogram. The conversion of substrate was 87%, the selectivity to BTX aromatics was 83%, and the yield of carbon as BTX aromatics was 72%.

TABLE IX-1

| Examples | Substrate | Catalyst | Conversion/% | Selectivity to BTX/% |
|---|---|---|---|---|
| 1 | Levulinic acid | WO$_3$/ZrO$_2$ | 97 | 93 |
| 2 | Acetoacetic acid | WO$_3$/ZrO$_2$ | 91 | 92 |
| 3 | Levulinic acid | WO$_3$/ZrO$_2$ | 86 | 86 |
| 4 | Ethyl acetoacetate | MoO$_3$/ZrO$_2$ | 99 | 89 |
| 5 | Methyl levulinate | CeO$_2$/ZrO$_2$ | 82 | 94 |
| 6 | Methyl acetobutyrate | WO$_3$/ZrO$_2$ | 93 | 83 |
| 7 | Octyl levulinate | MoO$_3$/ZrO$_2$ | 95 | 85 |
| 8 | Ethyl levulinate | La$_2$O$_3$/ZrO$_2$ | 93 | 85 |
| 9 | Butyl levulinate | WO$_3$/ZrO$_2$ | 93 | 87 |
| 10 | Ethyl levulinate | WO$_3$/ZrO$_2$ | 99 | 83 |
| 11 | Decyl levulinate | MoO$_3$/ZrO$_2$ | 96 | 84 |
| 12 | Methyl levulinate | MnO$_2$/ZrO$_2$ | 87 | 83 |

Although the embodiments of the present invention have been illustrated in detail above referring to the Examples, it should be understood that the protection scopes of the present invention are no restricted thereto; instead, the protection scopes are defined by the claims attached. Those skilled in the art can make appropriate modification to these embodiments without departing the technical idea and spirit of the invention, while the modified embodiments are also included within the protection scopes of the invention obviously.

The invention claimed is:

1. A process for producing aromatics, comprising a step of contacting an oxygen-containing raw material with an aromatization catalyst, under aromatization reaction conditions, to produce aromatics, wherein the oxygen-containing raw material has the structural formula (I):

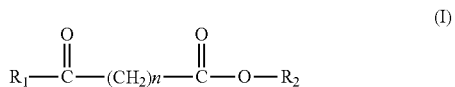

in formula (I), R$_1$ is selected from the group consisting of optionally substituted C$_{1-8}$ linear or branched alkyl, R$_2$ is selected from the group consisting of hydrogen and optionally substituted C$_{1-10}$ linear or branched alkyl, n is a positive integer of 1 to 6,
wherein the aromatization catalyst is one or more selected from the group consisting of molecular sieve, solid super acid, and composite metal oxide, wherein the molecular sieve is ZSM-type molecular sieve, wherein the ZSM-type molecular sieve is M/ZSM-5 molecular sieve, wherein M is selected from the group consisting of Zn, Ga, Sn, and a combination thereof.

2. The process according to claim 1, wherein the aromatization reaction conditions comprise: a reaction temperature of 300 to 800 degrees C., a reaction pressure of 0.1 to 10.0 MPa, a hydrogen pressure of 0.1 to 5 MPa, in gage pressure, and a WHSV of oxygen-containing raw material of 0.3 to 10 hour$^{-1}$.

3. The process according to claim 1, wherein the oxygen-containing raw material is derived from one or more selected from the group consisting of xylitol, glucose, cellobiose, cellulose, hemicellulose and lignin, or derived from one or more of paper manufacture sludge, waste paper, bagasse, glucose, wood, corn cob, corn stover, and straw stover.

4. The process according to claim 1, wherein the molecular sieve is a molecular sieve composition that comprises:
   a) 20 to 80 parts by weight of the molecular sieve,
   b) 20 to 80 parts by weight of a binder,
   c) 0 to 10 parts by weight of an auxiliary, wherein the auxiliary is one or more selected from the group consisting of Na, Ca, K, Be, Mg, Ba, V, Nb, Cr, Mo, W, Mn, Re, Fe, Co, Ni, Cu, Zn, Ga, Ru, Pd, Pt, Ag, B, Al, Sn, P, Sb, La, and Ce.

5. The process according to claim 1, wherein the ZSM-type molecular sieve has a molar ratio of Si to Al, calculated as $SiO_2/Al_2O_3$=10 to 500.

6. The process according to claim 1, wherein the solid super acid is one or more selected from the group consisting of Lewis acid supported solid super acid, inorganic metal salt/Lewis acid composite, and sulfated metal oxide.

7. The process according to claim 6, wherein the support of the Lewis acid supported solid super acid is one or more of selected from the group consisting of solid oxide of an element from Group IIIA of the periodic table of elements and solid oxide of an element from Group IVA of the periodic table,
   the Lewis acid in the Lewis acid supported solid super acid is one or more selected from the group consisting of halide of an element from Group VB, and halide of an element from Group IIIA and halide of an element from Group VA of the periodic table of elements,
   the inorganic metal salt in the inorganic metal salt/Lewis acid composite is one or more selected from the group consisting of inorganic acid salt of a metal element from Group IB, inorganic acid salt of a metal element from Group IIB, inorganic acid salt of a metal element from Group VII, and inorganic acid salt of a metal element from Group VIII of the periodic table of elements,
   the Lewis acid in the inorganic metal salt/Lewis acid composite is one or more selected from the group consisting of halide of an element from Group VB, halide of an element from Group IIIA, and halide of an element from Group VA of the periodic table of elements,
   the metal oxide in the sulfated metal oxide is oxide A of a metal element from Group IVB of the periodic table of elements or is oxide B obtained by modifying the oxide A with one or more modifying elements selected from the group consisting of metal element from Group IIIA (in the form of oxide), metal element from Group VIIB (in the form of oxide), noble metal element from Group VIII (in the form of metal elementary substance), base metal element from Group VIII (in the form of oxide), metal element from Group VIB (in the form of oxide), and lanthanide metal element (in the form of oxide) of the periodic table of elements.

8. The process according to claim 7, wherein, in the Lewis acid supported solid super acid, the Lewis acid is supported in an amount of 1 to 30 wt %, preferably 1 to 15 wt %,
   in the inorganic metal salt/Lewis acid composite, the weight ratio between the inorganic metal salt and the Lewis acid is 1-30:100,
   in the sulfated metal oxide, the metal oxide has a sulfated rate of 0.5-25 wt %,
   in the oxide B, the weight ratio of the modifying element in the form of oxide (calculated as oxide) to the oxide A is 0.1-25:100, and the weight ratio of the modifying element in the form of metal elementary substance (calculated as metal) to the oxide A is 0.1-15:100.

9. The process according to claim 1, wherein the composite metal oxide is a composite of oxide C and one or more oxide D, wherein oxide C is a metal element from Group IVB of the periodic table of elements, and oxide D is selected from the group consisting of oxide of a metal element from Group IIIA, oxide of a metal element from Group VII, oxide of a metal element from Group VIB and lanthanide metal element of the periodic table of elements.

10. The process according to claim 9, wherein a ratio of oxide C to oxide D is 60-99.9:0.1-40, calculated in parts by weight.

11. The process according to claim 1, further comprising a step of catalytically converting the biomass material to provide the oxygen-containing raw material.

12. A process for producing p-xylene, comprising the steps of: producing an aromatics product stream according to claim 1; and separating p-xylene from the aromatics product stream.

13. A process for producing terephthalic acid, comprising the steps of: producing an aromatics product stream according to claim 1; separating p-xylene from the aromatics product stream; and converting p-xylene into terephthalic acid.

14. The process according to claim 1, wherein $R_1$ is methyl, $R_2$ is selected from the group consisting of hydrogen and optionally substituted $C_{1-5}$ linear or branched alkyl, and n is 2.

15. The process according to claim 2, wherein the reaction temperature ranges from 300 to 650 degrees C., the reaction pressure ranges from 0.5 to 6.0 MPa, the hydrogen pressure ranges from 0.5 to 4 MPa, and the WHSV of oxygen-containing raw material ranges from 0.3 to 5 hour$^{-1}$.

16. The process according to claim 1, wherein the molecular sieve composition comprises:
   a) 30 to 70 parts by weight of the molecular sieve,
   b) 30 to 70 parts by weight of the binder, and
   c) 0.01 to 6 parts by weight of the auxiliary, wherein the auxiliary is one or more selected from the group consisting of Na, Ca, K, Be, Mg, Ba, V, Nb, Cr, Mo, W, Mn, Re, Fe, Co, Ni, Cu, Zn, Ga, Ru, Pd, Pt, Ag, B, Al, Sn, P, Sb, La, and Ce.

17. The process according to claim 4, wherein the binder is one or more selected from the group consisting of silica sol, pseudo-boehmite, alumina, acid treated clay, kaolin, montmorillonite, and bentonite, and/or wherein the auxiliary is one or more selected from the group consisting of Zn, Ga, and Sn.

18. The process according to claim 5, wherein the ZSM-type molecular sieve has $SiO_2/Al_2O_3$=15 to 200.

19. The process according to claim 7, wherein the support of the Lewis acid supported solid super acid is one or more selected from the group consisting of $SiO_2$, $B_2O_3$, and $Al_2O_3$,
   the Lewis acid in the Lewis acid supported solid super acid is one or more selected from the group consisting of $PF_3$, $AsF_3$, $SbF_3$, $BiF_3$, $SbF_5$, $TaF_3$, $VF_3$, and $NbF_3$,
   the Lewis acid supported solid super acid is one or more selected from the group consisting of $SbF_5/SiO_2$—$Al_2O_3$, $PF_3/Al_2O_3$—$B_2O_3$, $AsF_3/Al_2O_3$—$B_2O_3$, $SbF_3/Al_2O_3$—$B_2O_3$, $BiF_3/Al_2O_3$—$B_2O_3$, $TaF_3/Al_2O_3$—$B_2O_3$, $VF_3/Al_2O_3$—$B_2O_3$ and $NbF_3/Al_2O_3$—$B_2O_3$,
   the inorganic metal salt in the inorganic metal salt/Lewis acid composite is $CuCl_2$,
   the Lewis acid in the inorganic metal salt/Lewis acid composite is $AlCl_3$, and the sulfated metal oxide is oxide B obtained by modifying the oxide A with one or more selected from the group consisting of Fe, Pt, Re, Al, W, Cr, Mo, and Mn.

20. The process according to claim 7, wherein the support of the Lewis acid supported solid super acid is one or more of selected from the group consisting of $SiO_2$, $B_2O_3$ and $Al_2O_3$, the Lewis acid supported solid super acid is one or more selected from the group consisting of $SbF_5/SiO_2$—$Al_2O_3$, $PF_3/Al_2O_3$—$B_2O_3$, $AsF_3/Al_2O_3$—$B_2O_3$, $SbF_3/Al_2O_3$—$B_2O_3$, $BiF_3/Al_2O_3$—$B_2O_3$, $TaF_3/Al_2O_3$—$B_2O_3$, $VF_3/Al_2O_3$—$B_2O_3$, and $NbF_3/Al_2O_3$—$B_2O_3$, and the sulfated metal oxide is one or more selected from the group consisting of $SO_4^{2-}/ZrO_2$, $S_2O_8^{2-}/ZrO_2$, $SO_4^{2-}/TiO_2$, $SO_4^{2-}/ZrO_2$—$Fe_3O_4$, $Pt/SO_4^{2-}/TiO_2$, $SO_4^{2-}/TiO_2$—$ZrO_2$, $SO_4^{2-}/TiO_2$—$Al_2O_3$, $SO_4^{2-}/TiO_2$—$WO_3$, $SO_4^{2-}/ZrO_2$—$Fe_2O_3$—$Cr_2O_3$, $SO_4^{2-}/ZrO_2$—$WO_3$, $SO_4^{2-}/TiO_2$—$MoO_3$, and $SO_4^{2-}/ZrO_2$—$Fe_2O_3$—$MnO_2$.

21. The process according to claim 8, wherein in the Lewis acid supported solid super acid the Lewis acid is supported in an amount of 1 to 15 wt %, relative to the weight of the support, in the inorganic metal salt/Lewis acid composite the weight ratio between the inorganic metal salt and the Lewis acid is 1-15:100, in the sulfated metal oxide the metal oxide has a sulfated rate of 1-8 wt %, in the oxide B the weight ratio of the modifying element in the form of oxide (calculated as oxide) to the oxide A is 0.5-10:100, and the weight ratio of the modifying element in the form of metal elementary substance (calculated as metal) to the oxide A is 0.3-6:100.

22. The process according to claim 9, wherein oxide C is one or more selected from the group consisting of $ZrO_2$ and $TiO_2$ and, and oxide D is one or more selected from the group consisting of $B_2O_3$, $Al_2O_3$, $MnO_2$, $Cr_2O_3$, $CrO_3$, $MoO_3$, $WO_3$, $La_2O_3$, and $CeO_2$.

23. The process according to claim 22, wherein oxide C is $ZrO_2$, and oxide D is one or more selected from the group consisting of $MnO_2$, $MoO_3$, $WO_3$, $La_2O_3$, and $CeO_2$.

24. The process according to claim 10, wherein the ratio of oxide C to oxide D is 60-99.9:0.1-40, calculated in parts by weight.

* * * * *